(12) United States Patent
Schubert et al.

(10) Patent No.: US 10,588,896 B2
(45) Date of Patent: Mar. 17, 2020

(54) AGENTS FOR THE TREATMENT OF RETROVIRAL INFECTIOUS DISEASES

(71) Applicant: IMMUNOLOGIK GMBH, Trockenborn-Wolfersdorf (DE)

(72) Inventors: Ulrich Schubert, Trockenborn-Wolfersdorf (DE); Christian Setz, Memmelsdorf (DE); Wolfgang Brysch, Berlin (DE); Jörg Von Wegerer, Berlin (DE)

(73) Assignee: IMMUNOLOGIK GMBH, Trockenborn-Wolfersdorf (DE)

( * ) Notice: Subject to any disclaimer, the term of this patent is extended or adjusted under 35 U.S.C. 154(b) by 391 days.

(21) Appl. No.: 15/324,576

(22) PCT Filed: Jul. 10, 2015

(86) PCT No.: PCT/DE2015/000357
§ 371 (c)(1),
(2) Date: Jan. 6, 2017

(87) PCT Pub. No.: WO2016/004917
PCT Pub. Date: Jan. 14, 2016

(65) Prior Publication Data
US 2017/0202814 A1 Jul. 20, 2017

(30) Foreign Application Priority Data
Jul. 10, 2014 (DE) .......... 10 2014 010 220

(51) Int. Cl.
| | |
|---|---|
| *A61K 31/44* | (2006.01) |
| *A61K 31/69* | (2006.01) |
| *A61K 38/06* | (2006.01) |
| *A61K 45/06* | (2006.01) |
| *A61K 9/00* | (2006.01) |
| *C07D 213/73* | (2006.01) |

(52) U.S. Cl.
CPC ............ *A61K 31/44* (2013.01); *A61K 9/0053* (2013.01); *A61K 31/69* (2013.01); *A61K 38/06* (2013.01); *A61K 45/06* (2013.01); *C07D 213/73* (2013.01); *Y02A 50/481* (2018.01)

(58) Field of Classification Search
None
See application file for complete search history.

(56) References Cited

U.S. PATENT DOCUMENTS

2011/0305749 A1* 12/2011 Duch .................. C07K 14/005
424/450

OTHER PUBLICATIONS

Ericsson et al., Identification of receptors for pig endogenous retrovirus, 2003, PNAS, vol. 100, No. 11, pp. 6759-6734. (Year: 2003).*
Kassiotis et al., Making a virtue of necessity: the pleiotropic role of human endogenous retroviruses in cancer, 2017, Phil. Trans. R. Soc. B, vol. 372, 20160277,pp. 1-11. (Year: 2017).*
Fuerst et al., Designing a B Cell-based vaccine against a highly variable hepatitis C virus, 2018, Frontiers in Microbiology, vol. 8, Article 2692, pp. 1-11. (Year: 2018).*
Ali et al. (USP7 deubiquitinase controls HIV-1 production by stabilizing Tat protein. Biochem J. May 4, 2017;474(10):1653-1668. doi: 10.1042/BCJ20160304). (Year: 2017).*
International Search Report and Written Opinion dated Oct. 29, 2015 in corresponding International Application No. PCT/DE2015/000357.

* cited by examiner

*Primary Examiner* — Jeffrey S Lundgren
*Assistant Examiner* — William Y Lee
(74) *Attorney, Agent, or Firm* — Marilyn M. Brogan; Haug Partners LLP

(57) ABSTRACT

The invention relates to pyridine-3,5-bis-thiocyanates which are new active substances for the treatment and prevention of retroviral infections and secondary diseases thereof, in particular HIV infections and AIDS, from the group of deubiquitinase inhibitors. Administration of the compounds of the invention increases the immunogenicity of viral proteins and thus the antiviral response.

3 Claims, 15 Drawing Sheets

Figure 1:
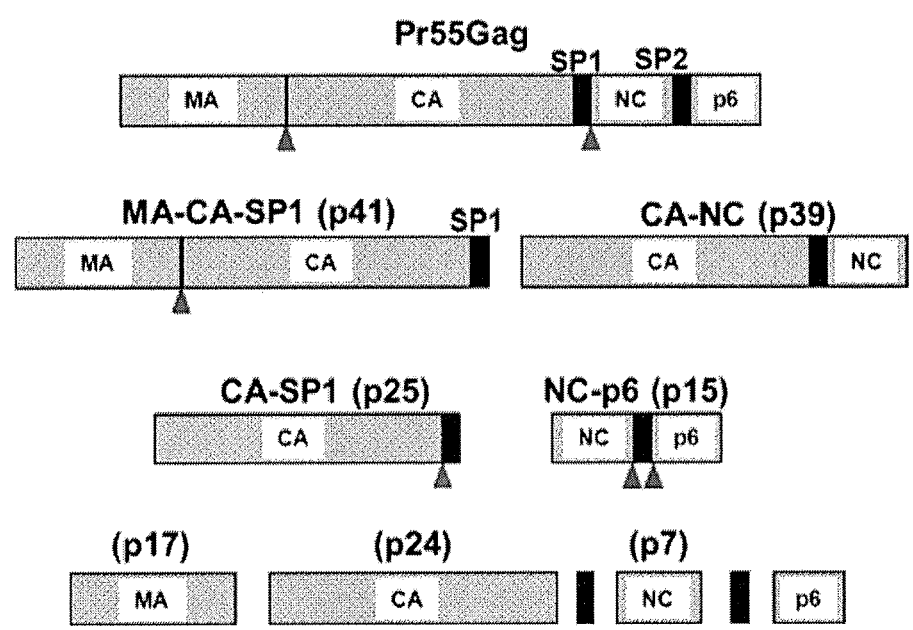

A.

B.

A.

B.

A.

B.

A.

B.

C.

A.

B.

C.

AGENTS FOR THE TREATMENT OF RETROVIRAL INFECTIOUS DISEASES

CROSS-REFERENCE TO RELATED APPLICATIONS

This application is the National Stage entry under 35 U.S.C. § 371 of International Application No. PCT/DE2015/000357 filed on Jul. 10, 2015, published on Jan. 14, 2016 under Publication Number WO 2016/004917, which claims the benefit of priority under 35 U.S.C. § 119 of German Patent Application Number 10 2014 010 220.3 filed Jul. 10, 2014.

The present invention relates to novel pharmaceutical agents for the treatment and prophylaxis of retroviral infectious diseases. Moreover, a new mode of action is disclosed.

Retroviral infections and the primary and secondary diseases resulting thereof constitute an important and often threatening part of viral infectious diseases. A well-known example is the infection with the Human Immunodeficiency Viruses type 1 and type 2 (HIV-1/HIV-2) and the outbreak of the Acquired Immunodeficiency Syndrome (AIDS) in patients caused thereby. Also tumors such as lymphomas and sarcomas can be caused by retroviruses.

Retroviruses integrate their genetic information in the genome of a host cell in order to reproduce themselves. In the virus, the genome is present in form of a single-stranded RNA. For integrating it into the genome of the host cell, it has to be transcribed before into cDNA by means of the enzyme reverse transcriptase. Previous treatment attempts focused always on an interaction with reverse transcriptase (RT) or with the retroviral proteins responsible for reproduction such as protease (PR) or integrase (IN). With the present invention it can be shown that also regulatory proteins of the host cell can be a promising target.

Since the beginning of the 1980ies the AIDS pandemic has confronted millions of HIV-infected humans with a multi-systemic and until now incurable disease. Originally, the course of this disease was lethal in most cases. Nowadays, a medical treatment option is provided, the highly active antiretroviral therapy (HAART; disclosed in WO 00/33654). It enables the survival of the patients when applied during lifetime, at least in the industrial countries, so that an HIV infection, respectively AIDS, has become a chronic disease. If this therapy fails, the course is still lethal. However, HAART is expensive and causes serious side effects. Further, the therapy is limited by the fact that HIV-1 displays an enormous mutation rate that is up to $10^6$ times higher in comparison with mutations within the human DNA. The polymorphism caused thereby leads invariably and in a relatively short time to the appearance of mutant HIV-1 forms that are resistant against single or even combined anti-HIV therapeutics such as HAART. Because of this high risk of resistances, the therapy resistance of certain patients as well as the serious side effects, there is a high medical need to develop new pharmaceutical agents for the HIV therapy. Therefore, it is the task of the present invention to provide such new pharmaceutical agents. It would be particularly advantageous if new cellular targets could be identified.

The task is solved by the compounds described by the general formula (I). Further advantageous embodiments are disclosed in the subclaims.

Human Immunodeficiency Viruses type 1 (HIV-1) belongs to the family of retroviruses (genus: lentiviridae). The HIV-1 genome has a length of ca. 9 kbp and has three open reading frames, Gag (group-specific antigens), Pol (PR, RT, integrase (IN)) and Env (glycoproteins gp41 and gp120, envelope glycoproteins). Additionally to these proteins canonically present in all retroviruses, HIV-1 encodes for six further regulatory proteins. Tat and Rev are essential for the viral replication. The accessory proteins Nef, Vpr, Vif and Vpu are not necessarily needed for the replication in cell culture but play an important role in vivo.

The main components of the HIV structural proteins are translated in form of three polyproteins: Gag and Gag-Pol include the inner core proteins and viral enzymes, whereas Env comprises the viral envelope proteins. Membrane-targeting signals in the $NH_2$-terminal domain of Gag are crucial for the transport of Gag to the cell membrane. The HIV-1 Gag polyprotein Pr55 is processed post-translationally by proteolysis into matrix (MA), capside (CA), nucleocapside (NC) and the COOH-terminal protein p6. During a process called budding, non-infectious virus particles are detached from the plasma membrane. Immediately after or even during budding and after the activation of viral protease proteolytic processing of Gag and Gag-Pol polyproteins starts. The proteolytic maturation of the virions is accompanied by morphologic changes. Characteristic for this is the condensation of the inner core that results in the formation of a cone-shaped core cylinder typical for the mature virus.

Proteasomes are multi-catalytic enzyme complexes accounting for ca. 1% of total cell protein. They represent the main proteolytic component in the cellular nucleus and the cytosol of eukaryotic cells. Proteasomes play many important roles in the cellular metabolism. The major function is the proteolysis of misfolded, non-functional proteins. Another important function is the degradation of cellular and viral proteins for the T cell-mediated immune response by the generation of peptide ligands which are loaded onto MHC-I molecules (MHC=major histocompatibility complex). A subform is the immunoproteasome that is constitutively expressed in specific cell types, for example in the spleen, lymph nodes and antigen-presenting cells.

Substrates of proteasomes are usually marked for degradation by the attachment of ubiquitin oligomers. Ubiquitin (Ub) is a highly conserved, 76 amino acid long protein that is covalently coupled to the respective target protein. Ubiquitinylation is a reversible process. Ub molecules can be removed from the target protein by numerous DUBs (deubiquitinating enzymes). Thus, Ub molecules are again intracellularly available. This recycling process is essential for cell homeostasis. This regulatory system of ubiquitinylation of target proteins and proteasomal proteolysis is usually referred to as ubiquitin proteasome system (UPS).

DUBs are a broad class of Ub hydrolases and are the intracellular opponents of ubiquitin E3 ligases. The target proteins can be deubiquitinated completely or partially. In humans, 90 DUBs are known until now, which are subdivided into five families:

ubiquitin-specific protease family (USP)
ubiquitin C-terminal hydrolases (UCHs)
ovarian tumor proteases (OTUs)
Josephin family
JAB1/MPN/Mov34 family (JAMMs)

The first four are cysteine proteases while the last one is a zinc metalloprotease.

The most important cellular functions of DUBs are:

1. They are crucial for the new generation of free ubiquitin. Ubiquitin is a linear fusion protein encoded on several genes and consisting of a row of Ub monomers. After translation this ubiquitin chain is specifically hydrolyzed by DUBs so that a release of free Ub molecules is effected.

2. They remove in a highly specific manner polyubiquitin chains of post-translationally modified proteins. Thus, the target protein is stabilized. Furthermore, the DUBs POH1, UCH37 and USP14 that are associated with the proteasome remove the ubiquitin chains from proteins that have already entered the proteasome for proteolysis. This way the content of free ubiquitin is kept in balance in the cell.

3. They alter the ubiquitin modifications of proteins by trimming the existing ubiquitin chains. For example, an originally polyubiquitinated protein can bear only a single ubiquitin in the end. Thereby, the function of the protein may be completely different.

In most cases DUBs show a high specificity for certain substrates as well as for specific ubiquitin chains.

DUBs, however, undergo themselves a complex regulation. Thus, post-translational modifications such as phosphorylation, ubiquitination or sumoylation may occur, leading to the activation or deactivation of the respective DUBs.

Also DUBs can undergo a conformational change by binding to certain proteins. This can also lead to the activation or deactivation of the respective DUBs.

Certain DUBs are limited in their activity to certain cell compartments. If needed, they are transported there.

Thus, DUBs are an interesting target for influencing cellular regulatory process through their inhibition or the modification of their activity. Also for clinical applications the whole UPS has moved into the focus in the last years. For example, there were attempts in the last years to inhibit components of the UPS such as the 26S proteasome or Ub ligases by means of small molecules. The rationale therefor was above all to find new therapeutic approaches for tumors. The only medication hitherto approved is the proteasome inhibitor Bortezomib (Velcade®) for the treatment of myelomas and T cell lymphomas. The mechanism of action, however, is not specific. The global effectiveness concerns numerous vital processes causing partially serious side effects such as the manifestation of a peripheral neuropathy with pain and numbness particularly in the extremities. In the clinical development of E3 ligase inhibitors there is no breakthrough until now.

Also in the investigation of DUB inhibitors, the development of new therapeutic approaches in tumor treatment is in the focus of interest. The DUB inhibitors known until now act in general highly specifically on a certain DUB target. Therefore, they display a relatively low cytotoxicity. Clearly less and milder side effects in patients are expected than in the use of 26S proteasome or E1 ligase inhibitors.

For some DUBs oncogenic properties have been shown, for example for USP2a, USP7, USP20 and USP33. Thus the inhibition of DUBs as a mode of action is regarded as a method for blocking or at least reducing the oncogenic properties of these DUBs.

The DUB inhibitor WP1130 effects a downregulation of anti-apoptotic genes and an upregulation of pro-apoptotic genes such as MCL-1 and p53. This induces apoptosis in tested tumor cell lines (Bartholomeusz et al., 2007, Blood 109(8), 3470-3478; Kapuria et al., 2010, Cancer Res 70(22). 9265-9276).

In CB-17 mice the use of the DUB inhibitor P005091 leads to apoptosis in multiple myeloma cells. A development of resistance under Bortezomib could thus be reverted (Chauhan et al., 2012, Cancer Cell 22(3), 345-358).

b-AP15 (a DUB inhibitor specific for UCH37/Uph-L5 and USP14) is able to inhibit tumor progression in different in vivo murine tumor models. Herein a daily injection of 5 mg/kg body weight was tolerated by the mice (D'Arcy et al., 2011, Nat Med 17(12), 1636-1640).

It could be shown in 2012 that it is possible to inhibit the replication of noro-, encephalyomyocarditis and sindbis virus in vitro using the DUB inhibitor WP1130 (Perry et al., 2012, PLoS Pathog 8(7):e1002783).

The virus families investigated in this publication are significantly different from the retrovirus family. Noroviruses belong to the family of caliciviridae, encephalomyocarditis viruses belong to the family of picornaviridae and sidbis viruses belong to the genus of alphaviridae. After infection, these virus families do not cause immunodeficiency in humans. In contrast to a retroviral infection no integration of the virus genome into the host genome takes place. Furthermore, the pathologic mechanism of these viruses is clearly different from retroviruses. Therefore, the medical need in these infections is significantly less than for retroviruses. Thus, no medication-based therapy has been developed to inhibit the replication of noro-, encephalyomyocarditis and sindbis viruses.

Noroviruses cause in general a viral gastroenteritis in humans which subsides in most cases after three days and in general shows no complications. Encephalyomyocarditis viruses are not pathogenic in humans and cause no disease in humans. Noroviruses as well as encephalyomyocarditis viruses are non-enveloped RNA viruses, in contrast to retroviruses. In infections with sindbis viruses in most cases a harmless febrile disease with inflammation of the joints occurs in rare cases that will quickly subside again. In contrast, a HIV-1 infection and the immunodeficiency resulting thereof leads nearly always to death without an antiretroviral treatment with ART.

Surprisingly, it could be shown that the inventive compounds according to the general formula (I) are able to inhibit late processes in the replication cycle of retroviruses.

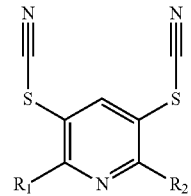

formula (I)

wherein $R_1$ and $R_2$ each independently from one another is —H, —OH, —NHR$_3$, —NR$_3$R$_4$, a substituted or non-substituted linear or branched alkyl residue with 1 to 3 carbon atoms, —CO—OCH$_3$, —CO—OC$_2$H$_5$, —CO—NH$_2$, —NH$_2$, —NO$_2$, —Cl, —Br, —F, —SO$_2$H;

$R_3$ and $R_4$ each independently from one another is —OH, —CH$_3$, —C$_2$H$_5$, —CH$_2$OH, —CHO, —COOH, —CO—CH$_3$, —CO—NH$_2$.

It is preferred that $R_1$ and $R_2$ each independently from one another is —H, —OH, —NH$_2$, —NO$_2$, —Cl, —F, —SO$_2$H.

In a particularly preferred embodiment $R_1$ and $R_2$ are —NH$_2$, respectively.

A particularly preferred embodiment is known under the name 2,6-diaminopyridine-3,5-bis(thiocyanate) or PR-619 (formula II). As the international nomenclature is not unitary, PR-619 is also known under the name 3,5-dithiocyanatopyridine. In the sense of this application all three names shall be used synonymously and refer to the same compound.

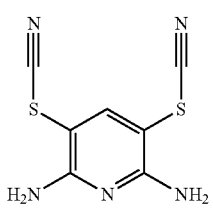

formula (II)

The invention relates also to all salts, hydrates, solvates and the salts of the hydrates and solvates of the inventive compounds. Suitable salts will be mentioned further below.

A synthesis route for PR-619 and related compounds can be found in Beer et al. 2002, J. Am. Chem. Soc. 124, p. 9498-9509.

Based on Applicant's further investigations and comparative structural analyses, it is assumed that the crucial structure for the mode of action of PR-619 is the dithiocyanatopyridine scaffold, as described in the general formula (I). Therefore, it can be reasonably assumed that moderately substituted derivatives of PR-619 show a comparable effect in the sense of the invention. This is expressed in general formula (I) and its variable residues.

PR-619 is hitherto known as a new DUB inhibitor. This compound inhibits USP1, USP2, USP4, USP5, USP7, USP5, USP9X, USP10, USP14, USP15, USP16, USP19, USP20, USP22, USP24, USP28, USP47, USP48, UCH-L1, UCH-L3, UCH-L5/UCH37, ATXN3, BAP1, JOSD2, OTUD5, VCIP135 and YOD. The application of PR-619 leads to an increase in polyubiquitin chains (Altun et al., 2011, Chem Biol 18(11), 1401-1412). Also for another DUB inhibitor, P22077, an activation of the autophagy pathway could be shown (Seiberlich et al., 2013, Cell Biochem Biophys 67(1), 149-160). Until now the research on PR-619 has focused on investigations of tumor treatment, without a therapeutically useful anti-proliferative potential to be found until now.

In the present application it could be shown that PR-619 and its derivatives can effectively inhibit the proteolytic processing of Gag polyproteins by HIV-1 protease (see Example 1). As a consequence of this inhibition, the replication and thus the spreading of the infection of the HI virus is inhibited. As described before, the proteolytic processing of Gag is an essential step in the replication of retroviruses. If this step is inhibited, the replication of the viruses is effectively blocked (see Examples 2 and 10). Thus, the viral infection can be treated or at least the viral load can be strongly limited so that the endogenous immune system is significantly better enabled to control and to fight the viral infection.

This mechanism of proteolytic processing of Gag is common to all retroviruses. Thus, the compounds according to the invention are apt not only to inhibit the replication of HIV-1 but also in all other known retroviruses, in particular in those closely related to HIV-1 such as lentiviridae, HIV-2, feline immunodeficiency virus (FIV) and simian immunodeficiency virus (Sly).

Therefore, the treatment and prophylaxis of infections with HIV-1, HIV-2, FIV and SIV as well as the diseases becoming manifest thereof such as AIDS and AIDS sequelae with a compound according to the invention is particularly preferred. Most preferred is the treatment and prophylaxis of HIV-1 infections as well as AIDS and AIDS sequelae.

In Example 3 the described inhibitory effect of PR-619 is compared to further commercially available DUB inhibitors. The experimental design was the same as in Example 1. P005091 (1-[5-[(2,3-dichlorophenyl)thio]-4-nitro-2-thienyl]-ethanone) inhibits specifically USP7. It was described that P005091 induces apoptosis in tumor cell lines (Chauhan et al., 2012 Cancer Cell 22(3), 345-358). WP1130 ((2E)-3-(6-bromo-2-pyridinyl)-2-cyano-N-[(1S)-1-phenylbutyl]-2-propenamide) inhibits specifically USP9, USO5, USP1 and UCH37. WP1130 leads to an accumulation of polyubiquitinated p53, JAK2 and Bcr-Abl, and reduces the protein level of c-Myc and MCL-1 in tumor cell lines (Bartholomeusz et al., 2007, Blood 109(8), 3470-3478; Kapuria et al., 2010, Cancer Res 70(22), 9265-9276).

It could be shown that P005091 and WP1130 have no influence on the replication of the HI virus. P22077, however, shows an effect comparable to PR-619, it also blocks efficiently the HIV-1 replication and thus the spreading of the virus.

As stated before, the effect of PR-619 is due to an inhibition of a DUB pathway. PR-619 displays inhibitory effects on a number of DUBs (see above). It can be assumed that PR-619 acts via the same DUB target as P22077. P22077, however, is specific for USP7 and USP47. PR-619 inhibits among others also USP7 and USP47. The non-effective P005091, however, inhibits specifically USP7. Nor P005091 neither WP1130 inhibit USP-47. The inevitable conclusion is that the inhibitory effect of PR-619 on the HIV-1 replication must be effected via an inhibition of USP47. This is confirmed by the results with P22077. As the underlying proteolytic processing of the Gag protein takes place in all retroviruses in this form, this mode of action via an inhibition of USP47 must be therapeutically effective in the treatment and prophylaxis of all retroviral infections and their sequelae.

Such a specific action on USP47 is also supported by the fact that USP7 and USP47 differ significantly in their subcellular localization and thus also in their function. While USP7 is only found in the cell nucleus, USP47 is exclusively localized in the cytosol. USP7 mainly interacts with a number of tumor proteins and regulates cellular transcription factors. Moreover, it could be shown that USP7 plays an important role in adipogenesis (Gao et al., 2013, Nat Commun 4, 2656). USP7 interacts only with proteins localized in the cell nucleus or are transported there (Nicholson and Kumar, 2011, Cell Biochem Biophys 60, 61-68). For USP47 It could be shown that it interacts with Ub E3 ligase β-TRCP and thereby regulates cell growth and survival of the cell, and that it plays an important role in DNA repair mechanism (Parsons et al., 2011, Mol Cell 41, 609-615; Peschiaroli et al., 2010, Oncogene 29, 1384-1393).

As the virus assembly of HIV-1 does not take place in the cell nucleus but USP7 is exclusively located there, it can be assumed that USP7 has no role herein. Thus, the inhibition of HIV-1 replication according to the invention by the DUB inhibitor P22077—blocking USP7 as well as USP47—can be ascribed to a specific inhibition of USP47. Furthermore, we could show that the DUB inhibitor P005091 inhibiting specifically USP7 is not able to block HIV-1 replication.

Therefore, the present application also refers to a method for the treatment and prophylaxis of retroviral infections and their sequelae by administration of an USP47 inhibitor. Preferred is the therapeutic use of this method for the treatment of HIV-1 infections as well as the treatment and prophylaxis of AIDS and AIDS sequelae.

In Examples 4 and 11 it could be shown that the aforementioned effects of PR-619 are not due to unspecific cytotoxic effects. Over a treatment period of 15 days PR-619 does not show a substantial reduction in the percentage of surviving cells. Only with a much higher dose (28 µM) than the effective dose of 3.5 µM toxic effects emerge.

The comparison of DUB inhibitors P005091 and WP1130 showed that with P005091 no cytotoxic effects were observed. In contrast, with WP1130 for permanent treatment already in the lowest used concentration of 3 µM a reduction in living cells by 40% appeared.

Furthermore, it was found that the inventive use of PR-619 augments the immunogenicity of HIV-1 structural proteins. This phenomenon is observed in HIV-1-infected primary PBMC cultures and in human fibroblast cultures (HeLa cells) transfected with viral DNA. This was shown with immunologic methods. The treatment of HeLa cells with PR-619 leads to a dose-dependent increase of the MHC-I antigen presentation of epitopes stemming from HIV-1 structural proteins (see Example 5). This increased MHC-I antigen presentation leads also to a stronger activation of CD8$^+$ T cells what augments the elimination of infected cells through cell-mediated immunity. Thereby, cells specifically infected with HIV-1 could be quicker recognized and efficiently destroyed.

Thus, it can be assessed that PR-619 and its derivatives dose-dependently are able
  a) to block, respectively to reduce the proteolytic processing of Gag polyproteins through HIV-1 protease;
  b) to block, respectively to reduce the infectivity of released virions; and
  c) to increase the immunogenicity of viral structural proteins and linked to that a strongly improved cytotoxic CD8$^+$T cell response.

Therefore, PR-619 and its derivatives are suitable compounds for the therapeutic treatment of retroviral infections, in particular of HIV-1 infections, as well as for the prophylaxis and treatment of AIDS, AIDS sequelae and further retroviral sequelae.

Further particular advantages of the use of PR-619 and its derivatives are the comparatively low cytotoxicity, what enables an effective dosing of the pharmaceutical agent, and the expected low, respectively mild side effects in patients.

Moreover, it is particularly advantageous that through the mode of action—which is common to all retroviruses—via the inhibition of the proteolytic processing of Gag polyprotein the use of a single pharmaceutical agent is able to fight an entire spectrum of retroviral infections. This is of particular importance in the treatment of rare retroviral infections for which. because of the low number of incidences and/or the low commercial potential, the development of an individual antiretroviral agent would not be deemed to be profitable. Furthermore, infections with novel retroviruses can thus be treated therapeutically and prophylactically. Also in the case of an unclear diagnosis which retroviral infection exactly is manifested the use of the compounds according to the invention seems to be promising.

It is also advantageous that with the compounds according to the invention an alternative to HAART is provided which is structurally clearly different. This is of huge importance particularly in the light of the resistance problems with HIV.

The antiretroviral agents hitherto known (e.g. from HAART) all attack at the viral enzymes, above all at reverse transcriptase and protease. The compounds according to the invention, however, block specifically a mechanism of the host cell without damaging it cytotoxically. Until now, retroviruses, in particular the HI virus, could "adapt" comparatively quickly to the attacking pharmaceutical agents and develop resistances because of its high mutation rate. Thereby, ever the more therapy-refractory retroviral infections develop over time. Mutations in the HI virus are up to $10^6$ times more frequent than in humans. Thus, the compounds according to the invention promise a many times longer period of application than classical antiviral medications. The ubiquitin-proteasome system as an important intracellular regulatory mechanism has been conserved relatively strongly throughout evolution. Herein, successful mutations are not very likely to occur, as the host organism (the human) could not draw an evolutionary advantage from such a mutation. In contrast, the host organism is relieved from the burden of a retroviral infection, or is at least strongly alleviated.

Thus, the present application refers to compounds according to formula (I) for use in medicine. This includes the pharmaceutically acceptable salts, hydrates and solvates of the compounds according to the invention.

The present application refers likewise to the use of a compound according to formula (I) for the production of a pharmaceutical composition for the treatment and/or prophylaxis of retroviral infections and/or its sequelae.

Particularly preferred is the use of PR-619 in medicine in general and in particular for the production of a pharmaceutical composition for the treatment and/or prophylaxis of retroviral infections and/or its sequelae.

The same way of proteolytic processing of Gag structural proteins is common to all known retroviruses. Thus, by the use of DUB inhibitors according to the invention the same mechanism of action is activated in all retroviruses so that their replication can be successfully suppressed. Therefore, the compounds according to the invention are suitable to be applied therapeutically and prophylactically in retroviral infections and secondary diseases resulting thereof. The compounds according to the invention are able through their mode of action to suppress or at least strongly mitigate the spreading of retroviruses in the host organism (see Examples). Thus, the systemic spreading of a retroviral infection in the organism can be avoided. This way the compounds according to the invention can also be used for prophylaxis.

According to the present application the term HIV or HIV-1 virus shall comprise all groups and subtypes, in particular group M with subtypes A (A1-A4), B, C, D, E, F (F1-F2), G, H, I, J, K and the CRFs (circulating recombinant forms) as well as groups N, O and P.

HIV-2, Feline Immunodeficiency Virus (FIV) and Simian Immunodeficiency Virus (SIV) are structurally related to HIV-1.

An infection with HIV-1 or HIV-2 leads in most cases to an outbreak of AIDS if the patient is not treated in a suitable manner, e.g. with HAART. AIDS, however, often entails a number of sequelae.

Thus, the present invention refers likewise to the use of a compound according to formula (I) for the production of a pharmaceutical composition for use in the treatment and/or prophylaxis of a HIV-1 infection, HIV-2 infection, AIDS, AIDS sequelae, FIV infection and SIV infection.

Particularly preferred is the use of PR-619 for the production of a pharmaceutical composition for use in the treatment and/or prophylaxis of a HIV-1 infection, HIV-2 infection, AIDS, AIDS sequelae, FIV infection and SIV infection.

Moreover, a therapeutic or prophylactic use of the compounds according to the invention is possible in the following other retroviral groups: spuma viruses, in particular Simian Foamy Virus (SFV) and Bovine Foamy Virus (BFV); alpha retroviruses, in particular Rous Sarcoma Virus (RSV) and Avian Leucosis Virus; beta retroviruses, in particular Mouse Mammary Tumor Virus (MMTV) and Mason-Pfizer Monkey Virus (MPMV); gamma retroviruses, in particular Murine Leukemia Virus (MLV) and Feline Leukemia Virus (FeLV); delta retroviruses, in particular Bovine Leukemia Virus (BLV) and Human T-lymphotropic Virus (HTLV); epsilon retroviruses, in particular Walleye Dermal Sarcoma Virus (WDSV) and Walleye Epidermal Hyperplasia Virus (WEHV).

During the outbreak and progression of AIDS disease, multiple systemic sequelae can occur in humans that likewise may be life-threatening and restrict the life quality of the affected patients considerably. These could be treated above all symptomatically. For a causal therapy, however, the underlying HIV infection must be treated. Therefore, the compounds according to the invention are also suitable for a prophylactic or therapeutic use in the following AIDS sequelae: HIV-induced dementia, in particular caused by HIV infection of neurons, glial cells and endothelial cells in cerebral capillaries; HIV-induced nephropathy (HIVAN); AIDS-associated lipodystrophy; AIDS-associated pulmonary hypertension; bacterial, viral or fungal opportunistic infections such as candidose of the lower respiratory tract; chronic intestinal isosporiasis, chronic intestinal cryptosporidiosis, CMV (cytomegalovirus) infection, coccidioidomycosis, herpes simplex infection in the lung, bronchia or esophagus, histoplasmosis, cryptococcosis, esophageal candidose, *Pneumocystis carinii* (*jiroveci*) pneumonia, progressive multifocal leukoencephalopathy (PML), recurrent *Salmonella* sepsis, toxoplasmosis of the central nervous system, tuberculosis, nocardiosis, penicilliosis, aspergillosis, aphasia, hemianopsia, tumors such as anal carcinoma/anal cancer, Burkitt lymphoma, cervix carcinoma, Kaposi sarcoma, primary CNS lymphoma, encephalopathy, wasting syndrome.

Compounds of the invention according to the general formula (I) are also suitable for use together with at least one further active agent, wherein said further active agent is selected from a group comprising reverse transcriptase inhibitors, integrase inhibitors, HIV protease inhibitors, entry inhibitors, HIV vaccine, virostatic agents and immunostimulatory agents. Also a combination of at least one compound of the invention and at least one other inhibitor of cellular factors such as a proteasome inhibitor (PI) can be used. Studies for HIV treatment with PIs are already underway. Surprisingly, it was found that a combined application of the proteasome inhibitor bortezomib (Velcade®) (WO 02/059130 A1; WO 02/059131 A1) from the group of boronates and a compound of the invention according to general formula (I) inhibits the replication and thus the viral spreading of HIV-1 already at very low concentrations (Example 6). Herein, subthreshold concentrations of both substances, respectively, show a supra-additive effect in a combined application. A comparable effect after a combined application of the specific immunoproteasome inhibitor PR-957 (synonym: ONX-0914; WO 2007/149512 A1; Muchamuel et al., 2009, Nat Med 15, 781-787) from the group of epoxyketones and of an inventive compound according to general formula (I) could be observed already at very low concentrations (Example 8). Also herein the respective subthreshold concentrations of both substances show in a combined application a supra-additive effect. This is the more surprising since PR-619 as a DUB inhibitor and bortezomib or PR-957 as a proteasome inhibitor act at different parts of the UPS. Since the mechanism of action of all proteasome inhibitors is similar it can be reasonably assumed that also a combined application of a compound of the invention according to general formula (I) with another proteasome inhibitor will display a supra-additive effect on the inhibition of the infection spreading of HIV-1. Many of them have a huge structural similarity either with bortezomib or with PR-619.

Thus, the present application refers also to a combination of at least one compound of the invention according to general formula (I) and at least one proteasome inhibitor, preferred on a combination of at least one compound of the invention according to general formula (I) and bortezomib or PR-957, and particularly preferred on a combination of PR-619 and bortezomib as well on a combination of PR-619 and PR-957, and salts and hydrates of the aforementioned combinations.

Further not limiting examples for proteasome inhibitors are aldehydes such as MG-132, PSI, fellutamide B, delanzomib (CEP-18770), ixazomib (MLN9708), MLN2238, MLN9074; epoxyketones such as epoximicin, carfilzomib (PR-171), oproxomib (ONX-0912; PR-047), YU-101; α-ketoaldehyde proteasome inhibitors, beta-lactones such as omuralide, salinosporamide A, PS-519, marizomib (NPI-0052), belactosin A, belactosin C; vinyl sulfones such as $^{125}$1-NIP-LSCS, MV151; syrbactins such as SylA, GlbA; lactames such as lactacystin; peptides such as PR-39; bacteria-derived proteasome inhibitors such as TMC-95A, syringolin A, glidobactin A, HT1171, GLS; as well as chloroquine, 5-amino-8-hydroxyquinoline (SAHQ), clioquinol.

Furthermore, the present application refers to the aforementioned combination for use in medicine, in particular to the combination of PR-619 and bortezomib or PR-957 for use in medicine.

Thereby, synergistic effects in the treatment of retroviral infections can be attained. Another advantage is that in such a combination therapy low amounts of the single active agent, respectively, can be used, which can lead to a reduction of the agent-specific side effects, and possibly to a diminution of the hitherto considerable treatment costs of HIV patients. It were above all the severe side effects that strongly limited the therapeutic use of proteasome inhibitors until now. A further advantage is that with more than one mechanism of action the number of therapy-refractory patient will drop considerably. Moreover, with such a combination therapy, in which the anti-retroviral effect is mediated via different mechanisms of action, the risk of resistance development of the retrovirus, in particular of HIV, is diminished.

Reverse transcriptase inhibitors suitable for such a combination therapy are nucleoside reverse transcriptase inhibitors (NRTI) and non-nucleoside reverse transcriptase inhibitors (NNRTI). Examples of NRTI include, but are not limited to, Abacavir, Didanosine, Emtricitabine, Lamivudine, Stavudine, Tenofovir, Zidovudine, Zalcitabine, Entecavir, Adefovir, Elvucitabine, Fosalvudine(-tidoxil), Fozivudintidoxil, Lagiciclovir, Alamifovir, Clevudine, Pradefovir, Telbivudine. Examples of NNRTI include, but are not limited to, Efavirenz, Etravirine, Nevirapine, Rilpivirine, Delavirdine, Emivirine, Lersivirine.

Suitable for a combination therapy according to the invention are integrase inhibitors such as Raltegravir, Elvitegravir, Dolutegravir, MK-2048.

Examples of HIV protease inhibitors suitable for a combination therapy according to the invention are Saquinavir, Indinavir, Ritonavir, Nelfinavir, Amprenavir, Lopinavir, Atazanavir, Fosamprenavir, Tipranavir, Darunavir, Brecanavir, Mozenavir, Tipranavir.

Examples of entry inhibitors suitable for a combination therapy according to the invention are Enfuvirtid and Malaviroc.

General virostatic agents suitable for a combination therapy according to the invention can be selected from the group comprising Ancriviroc, Aplaviroc, Cenicriviroc, Enfuvirtide, Maraviroc, Vicriviroc, Amantadine, Rimantadine, Pleconaril, Idoxuridine, Aciciovir, Brivudine, Famciclovir, Penciclovir, Sorivudine, Valaciclovir, Cidofovir, Ganciclovir, Valganciclovir, Sofosbusvir, Foscarnet, Ribavirine, Taribavirine, Filibuvir, Nesbuvir, Tegobuvir, Fosdevirine, Favipiravir, Merimepodib, Asunaprevir, Balapiravir, Boceprivir, Ciluprevir, Danoprevir, Daclatasvir, Narlaprevir, Telaprevir, Simeprevir, Vanipevir, Rupintrivir, Fomivirsen, Amenamevir, Alisporivir, Bevirimat, Letermovir, Laninamavir, Oseltamivir, Peramivir, Zanamivir.

General immunostimulatory agents suitable for a combination therapy according to the invention can be selected from the group comprising interferons ($\alpha$-, $\beta$-, $\gamma$-, $\tau$-interferon), interleukins, CSF, PDGF, EGF, IGF, THF, Levamisol, Dimepranol, Inosine.

Furthermore, possible combinations according to the invention are PR-619 or one of its derivatives with adjuvants, such as Cobicistat.

It is particularly preferred if the compound according to the invention in the aforementioned combinations of active agents is PR-619.

The terms "medicine" or "medical" comprise human as well as veterinary medicine.

The term "organism" refers to a living being, especially a human or an animal, possessing a self-regulating immunological system.

The term "host organism" is used in terms of the application for those organisms exploited for replication by viruses, herein especially retroviruses, following an infection with them.

The term "active agent" in this application refers to compounds for use according to the invention according to general formula (I) and in particular to PR-619. Moreover, this term can comprise further pharmaceutical agents, known from the state of the art.

The terms "composition" and "pharmaceutical composition" comprise at least one active agent according to the general formula (I) in any pharmacologically suitable defined dose and dosage form together with at least one suitable excipient or carrier substance as well as all substances which are directly or indirectly generated as a combination, accumulation, complex formation or crystal of the aforementioned ingredients, or come into being as a result of other reactions or interactions as well as optionally at least one further pharmaceutical agent known in the state of the art.

The term "excipient" is used in this application to describe each component of a pharmaceutical composition in addition to the active agent. The selection of a suitable excipient depends on factors such as dosage form and dose as well as the influence on the solubility and stability of the composition by the excipient itself.

The term "action" describes the inherent specific mode of action of the respective agent in the scope of the present application.

The terms "effect", "therapeutic effect", "action", "therapeutic action" regarding at least one active agent according to the general formula (I) refer to causally occurring beneficial consequences for the organism, to which the at least one active agent has been administered.

In terms of the application, "therapeutically effective dose" means that a sufficient dose of the at least one active agent according to the general formula (I) is administered to a living being or to a patient in need of such a treatment.

The terms "joint administration", "combined administration" or "simultaneous administration" of at least one pharmaceutical agent according to the general formula (I) and/or of at least one pharmaceutical agent from the state of the art comprise the administration of the mentioned agents at the same time or at time points factually related close to each other, as well as administrations of said agents at different times within a coherent experiment. The chronological order of the administration of said agents is not limited by these terms. Those skilled in the art will have no difficulties to deduce the described administrations in respect to their chronological or local order from his knowledge and experience.

The term "living being" refers to every animal, especially vertebrate, including human. A "patient" in terms of the application is a living being who suffers from a definable and diagnosable disease, and to whom a suitable active agent can be administered.

The terms "prophylaxis", "treatment" and "therapy" comprise the administration of at least one suitable active agent according to the general formula (I), alone or in combination with at least one further pharmaceutical agent known in the art, to a living being, in order to prevent the development of a certain disease, to inhibit, and to alleviate the symptoms, or to initiate a healing process of the respective disease.

The compounds according to the invention can be provided as pharmaceutically acceptable salts of organic and inorganic acids. Suitable examples are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, digluconic acid, lactic acid, tartaric acid, hydroxymaleic acid, pyruvic acid, phenylacetic acid, benzoic acid, p-aminobenzoic acid, p-hydroxybenzoic acid, dinitrobenzoic acid, chlorbenzoic acid, methanesulfonic acid, ethanesulfonic acid, nitric acid, hydroxyethanesulfonic acid, ethylenesulfonic acid, p-toluylsulfonic acid, naphthylsulfonic acid, sulfanilic acid, camphorsulfonic acid, alginic acid, capric acid, hippuric acid, pectinic acid, phthalic acid, quinic acid, mandelic acid, o-methyl mandelic acid, hydrogen benzenesulfonic acid, picric acid, adipic acid, cyclopentane propionic acid, D-o-toluyl tartric acid, tartronic acid, benzenesulfonic acid, alpha-methyl benzoic acid, (o, m, p-)methyl benzoic acid, naphthylamine sulfonic acid, as well as salts from other mineral acids or carbonic acids well known to a person skilled in the art. These salts are generated by contacting the free base with a sufficient amount of the respective acid in order to build the salt in a conventional manner.

Pharmaceutically acceptable salts should be seen in terms of this application as an active agent containing a compound according to the invention in form of a salt, in particular if this salt bestows specific or ameliorated pharmacokinetic properties in comparison to the free form of the active agent or to another salt of the active agent. The pharmaceutically acceptable salt of the active agent may also bestow a pharmacokinetic characteristic to the active agent it did not have in its free form. Thus it may even positively influence the pharmacodynamics of the active agent in respect to its therapeutic efficacy in the organism.

The compounds according to the invention can also be provided as hydrates or solvates. In terms of this application solvates refer to such forms of the compounds according to the invention that build a complex through coordination with solvent molecules. Hydrates are a specific form of solvates in which the coordination is effected by water molecules.

The inventive compounds according to the general formula (I) can be chiral because of their molecular structure and thus may be present as enantiomers. They can be provided as a racemate or in an optically active form. Since the pharmaceutical efficacy of a racemate or of the stereoisomers of the compounds according to the invention may differ it can be desirable to use isolated enantiomers. In this case the final product or even an intermediate can be separated into its enantiomers by chemical or physical methods known by a person skilled in the art, or an enantiomer can already be used for synthesis.

In case of a racemate, diastereomers are built from the mixture by reacting them with an optically active separating agent. Suitable separating agents are e.g. optically active acids such as R- and S-forms of tartric acid, diacetyl tartric acid, dibenzoyl tartric acid, mandelic acid, malic acid, lactic acid, suitable N-protected aminoacids (e.g. N-benzoylproline or N-benzoylsulfonylproline) or different optically active camphorsulfonic acids. Advantageous is also a chromatographic separation of enantiomers by means of an optically active separating agent (e.g. dinitrobenzoyl phenylglycine, cellulose triacetate or other derivatives of carbohydrates or chirally derivatized methacrylate polymers fixated on silica). Suitable solvents therefor are aqueous or alcoholic solvent mixtures such as hexane/isopropanol/acetonitrile, e.g. in a ratio 82:15:3.

Pharmaceutical formulations of the compounds according to the invention can be administered by any suitable way, e.g. orally (incl. buccally and sublingually), rectally, vaginally, nasally, topically (incl. buccally, sublingually, conjunctivally or transdermally), or parenterally (incl. subcutaneously, intramuscularly, intravenously, intraarterially or intradermally).

Formulations can be produced by any method known in the pharmaceutical field by combining for example the active agent with (a) carrier(s) or (an) excipient(s).

The compounds according to the invention can be mixed with all carriers known in the art, in solid dosage forms for example plant and animal fats, waxes, paraffins, starch, tragacanth, cellulose derivatives, polyethylene glycols, silicones, bentonites, silica, talcum, zinc oxide or mixtures of the aforementioned substances. For liquid dosage forms and emulsions suitable carriers are for example solvents, solubilizing agents, emulsifiers such as water, ethanol, isopropanol, ethyl carbonate, ethyl acetate, benzyl alcohol, benzyl benzoate, propylene glycol, 1,3-butyl glycol, cotton seed oil, peanut oil, olive oil, castor oil, sesame oil, glycerol fatty acid esters, polyethyl glycols, fatty acid esters of sorbitan, or mixtures of the aforementioned substances. Suspensions according to the invention may use carriers known in the art such as diluents (e.g. water, ethanol or propylene glycol), ethoxylized isostearyl alcohols, polyoxyethylene and polyoxyethylene sorbitan esters, microcrystalline cellulose, bentonites, agar agar, tragacanth, or mixtures of the aforementioned substances.

Pharmaceutical formulations adapted for oral dosage forms may be administered as separate units such as capsules, tablets, sugar-coated tablets or pills; powders or granulates; juices, syrups, drops, teas, solutions or suspensions in aqueous or non-aqueous liquids; edible foams or mousses; or in oil-in-water lotions or water-in-oil in lotions.

For example, in an oral dosage form such as a tablet or capsule the active agent can be combined with an oral, non-toxic and pharmaceutically acceptable inert carrier such as ethanol, glycerin or water. Powders are produced by grinding the compound to a suitably tiny particle size and mixing them with a pharmaceutical carrier ground in a similar manner, e.g. an edible carbohydrate such as starch or mannitol. A flavor, preservative, dispersant or colorant can also be present.

Capsules can be produced by producing a powder mixture as described before and filling it into shaped gelatine covers. Glidants and lubricants such as highly dispersed silica, talcum, magnesium stearate, calcium stearate or polyethylene glycol can be added to the powder mixture as solids before the filling process. A disintegrant or solubilizer such as agar agar, calcium carbonate or sodium carbonate can be added likewise in order to improve the availability of the medication after intake of the capsule.

Additionally, suitable binding agents, lubricants, glidants and disintegrants as well as colorants can be added to the mixture, if desirable or necessary.

The term binding agents refers to substances that bind powders or glue them together, rendering them cohesive through granule formation. They serve as a "glue" of the formulation. Binding agents increase the cohesive strength of the provided diluent or filler.

Suitable binding agents are starch from wheat, corn, rice or potato, gelatine, naturally occurring sugars such as glucose, sucrose or beta-lactose, sweeteners from corn, natural and synthetic gums such as acacia, tragacanth or ammonium calcium alginate, sodium alginate, carboxymethyl cellulose, sodium carboxymethyl cellulose, hydroxypropyl carboxymethyl cellulose, polyethylene glycol, polyvinyl pyrrolidone, magnesium aluminium silicate, waxes and others. The percentage of the binding agent in the composition can range from 1-30% by weight, preferred 2-20% by weight, more preferred 3-10% by weight and most preferred 3-6% by weight.

The term lubricants refers to substances that are added to the dosage form in order to facilitate tablets, granulates etc. to be released from the press mold or the outlet nozzle after producing them by diminishing friction or abrasion. Lubricants are usually added shortly before pressing, as they should be present on the surface of the granules and between them and the parts of the press mold. The amount of the lubricant in the composition may vary between 0.05 and 15% per weight, preferred between 0.2 and 5% per weight, more preferred between 0.3 and 3% per weight, most preferred between 0.3 and 1.5% per weight.

Suitable lubricants to be used in these dosage forms are a.o. sodium oleate, metal stearates such as sodium stearate, calcium stearate, potassium stearate and magnesium stearate, stearic acid, sodium benzoate, sodium acetate, sodium chloride, boric acid, waxes having a high melting point, polyethylene glycol a.o.

Glidants are materials that prevent a baking of the respective agents and improve the flow characteristics of granulations so that the flow is smooth and constant.

Suitable glidants comprise silicon dioxide and talcum. The amount of the glidant in the composition may vary between 0.01 and 10% per weight, preferred between 0.1 and 7% per weight, more preferred between 0.2 and 5% per weight, most preferred between 0.5 and 2% per weight.

The term disintegrant refers to substances added to a composition in order to facilitate their breaking apart.

To the disintegrants belong, without being limiting, starch, cold water-soluble starches such as carboxymethyl starch, cellulose derivatives such as methyl cellulose and sodium carboxymethyl cellulose, microcrystalline cellulose and cross-linked microcrystalline celluloses such as croscarmellose sodium, natural and synthetic gums such as guar, agar, karaya, locust bean gum, tragacanth, clays such as bentonite, xanthan gum, alginates such as alginic acid and sodium alginate, foaming compositions a.o. The amount of the disintegrant in the composition may vary between 1 and 40% per weight, preferred between 3 and 20% per weight, most preferred between 5 and 10% per weight.

Colorants are excipients that bestow a colorization to the composition or dosage form. These excipients can be food colorants. They can be adsorbed on a suitable adsorption means such as clay or aluminium oxide. The amount of the colorant may vary between 0.01 and 10% per weight of the composition, preferred between 0.05 and 6% per weight, more preferred between 0.1 and 4% per weight, most preferred between 0.1 and 1% per weight.

Tablets are formulated by producing, granulating or dry-pressing a powder mixture, adding a lubricant and a disintegrant and pressing the mixture to a tablet. A powder mixture is produced by mixing a suitably ground compound with a diluent or a base as described before, and if applicable, with a binding agent such as carboxymethyl cellulose, an alginate, gelatine or polyvinyl pyrrolidone, a dissolution retardant, such as paraffin, an absorption accelerator, such as a quaternary salt, and/or an absorbent, such as bentonite, kaolin or dicalcium phosphate. The powder mixture can be granulated by wetting it with a binder, such as, for example, syrup, starch paste, mucilage (e.g. acacia) or solutions of cellulose or polymer materials and pressing it through a sieve. As an alternative to granulation, the powder mixture can be run through a tableting machine, giving lumps of non-uniform shape which are broken up to form granules. The granules can be lubricated by adding stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps.

Liquid dosage forms comprise solutions, suspensions and emulsions. Examples are water and water/propylene glycol solutions for parenteral injections, or the addition of a sweetener or opacifier for oral solutions, suspensions and emulsions. Liquid dosage forms may also comprise solutions for intranasal administration.

Moreover, buffer solutions can be parts of pharmaceutical compositions. The terms buffer, buffer system and buffer solution, in particular of an aqueous solution, refer to the capacity of the system to resist a pH change by the addition of an acid or a base, or by dilution with a solvent.

Buffer systems may be selected from the group comprising formate, lactate, benzoic acid, oxalate, fumarate, aniline, acetate buffer, citrate buffer, glutamate buffer, phosphate buffer, succinate, pyridine, phthalate, histidine, MES (2-(N-morpholino) ethanesulfonic acid), maleic acid, cacodylate (dimethyl arsenate), carbonic acid, ADA (N-(2-acetamido) imino diacetic acid), PIPES (4-piperazine-bis-ethanesulforiic acid), BIS-TRIS propane (1,3-bis[tris(hydroxymethyl) mehylaminol] propane), ethylene diamine, ACES (2-[(amino-2-oxoethyl)amino]ethanesulfonic acid), imidazol, MOPS (3-(N-morphino)-propanesulfonic acid), diethyl malonic acid, TES (2-[tris(hydroxymethyl)methyl]aminoethanesulfonic acid) and HEPES (N-2-hydroxyethylpiperazine-N'-2-ethanesulfonic acid), as well as other buffers with a pKa between 3.8 and 7.7.

Preferred are carbonic acid buffers such as acetate buffer and dicarboxylic acid buffers such as fumarate, tartrate and phthalate as well as tricarboxylic acid buffers such as citrate. A further group of preferred buffers are inorganic buffers such as sulfate hydroxide, borate hydroxide, carbonate hydroxide, oxalate hydroxide, calcium hydroxide and phosphate buffers. Still another group of preferred buffers are nitrogen-containing puffers such as imidazol, diethylene diamine and piperazine. Furthermore preferred are sulfonic acid buffers such as TES, HEPES, ACES, PIPES, [(2-hydroxy-1,1-bis-(hydroxymethyl)ethyl)amino]-1-propanesulfonic acid (TAPS), 4-(2-hydroxyethyl)piperazine-1-propanesulfonic acid (EEPS), 4-morpholino-propanesulfonic acid (MOPS) and N,N-bis-(2-hydroxyethyl)-2-aminoethanesulfonic acid (BES). Another group of preferred buffers are glycine, glycyl-glycine, glycyl-glycyl-glycine, N,N-bis-(2-hydroxyethyl)glycine and N-[2-hydroxy-1,1-bis(hydroxymethyl)ethyl]glycine (tricine). Preferred are also amino acid buffers such as glycine, alanine, valine, leucine, isoleucine, serine, threonine, phenylalanine, tyrosine, tryptophan, lysine, arginine, histidine, aspartate, glutamate, asparagine, glutamine, cysteine, methionine, proline, 4-hydroxyproline, N,N,N-trimethyllysine, 3-methyl histidine, 5-hydroxylysine, o-phosphoserine, gamma-carboxyglutamate, [epsilon]-N-acetyl lysine, [omega]-N-methyl arginine, citrulline, ornithine and their derivatives.

Preservatives for liquid dosage forms or supplements can be used on demand and are selected from potassium sorbate, methyl ethyl paraben, sodium benzoate and other substances or compositions thereof known to the person skilled in the art for this purpose.

A particularly preferred pharmaceutical composition is a lyophilisate (a dry-freezed formulation) suitable for administration via inhalation or intravenous injection. For its production, a compound for use according to the invention is solubilized in a 4-5% mannitol solution, whereupon this solution is lyophilized. The mannitol solution can be prepared in a suitable buffer solution, as described before. Further examples of suitable cryo/lyoprotectants (also fillers or stabilizers) are thiol-free albuminin, immunoglobulin, polyalkylene oxide (i.e. PEG, polypropylene glycol), trehalose, glucose, sucrose, sorbitol, dextran, maltose, raffinose, stachyose and other saccharides. Mannitol is preferred. They can be used in the lyophilization process in usual amounts known to a person skilled in the art.

For the production of a dosage form of a suppository with compounds according to the invention waxes with a low melting point as well as a mixture of fatty acid glycerides such as cocoa butter are first melted, then the active agent is homogenously dispersed therein under stirring or other mixing methods. The molten homogeneous mixture is transferred to suitable moulds and then cooled down and thus solidified.

For topical applications of the compounds according to the invention creams, emulsions, lotions, gels, pastes, ointments and suspensions are suitable.

Suitable as surface-active solubilizing agents (solubilizers) are for example diethylene glycol monoethyl ether, polyethyl propylene glycol co-polymers, cyclodextrins, glyceryl monostearates such as Solutol HS 15 (Macrogol-15-hydroxystearate from BASF, PEG 660-15 hydroxystearates), sorbitan esters, polyoxyethylene sorbitanic acid esters, polyvinyl alcohol, sodium dodecyl sulfate, (anionic) glyceryl monooleates etc.

Eligible as emulsifiers are for example from the following anionic and non-ionic emulsifiers: Anionic emulsifier waxes, cetyl alcohol, cetylstearyl alcohol, stearic acid, oleic acid, polyoxyethylene polyoxypropylene block polymers, addition products of 2 to 60 mol ethylene oxide to castor oil and/or hardened castor oil, wool wax oil (lanolin), sorbitan esters, polyoxyethylene alkyl esters, polyoxyethylene sorbitan fatty acid esters or polyvinyl alcohol. Preferred are glycerin monooleate, stearic acid and phospholipids such as lecithin.

Eligible as triglycerides are medium-chain and high molecular triglycerides. Medium-chain triglycerides are glycerin esters of fatty acids with only 6-12 carbon atoms, such as caprylic/capric acid triglyceride. High molecular triglycerides are glycerin fatty acid esters with long-chained fatty acids, e.g. triglyceride mixtures extracted from several naturally occurring fats. Preferred are medium-chain triglycerides, in particular caprylic/capric acid triglyceride.

Suitable permeation enhancers (penetration enhancers) are for example isopropyl myristate, oleic acid, sodium lauryl sulfate and 1,2-propanediol. Preferred is 1,2-propanediol.

Typical examples for preservatives suitable for topical applications are e.g. benzyl benzoate, benzoic acid, benzyl alcohol, benzalkonium chloride, N-cetyl-N—N-trimethyl-ammonium bromide (Cetrimid, Merck), chlorhexidine, chlorbutanol, chlorcresol, imiudurea, parabens such as methyl, ethyl, propyl or butyl paraben, sodium methylparaben, sodium propylparaben, potassium sorbate, sodium benzoate, sodium propionate, phenol, phenoxyethanol, phenylethyl alcohol, phenylmercuriacetate, phenylmercuriborate, phenylmercurinitrate, sorbic acid or Thiomersal (sodium methylmercurithiosalicylate). Preferred are methylparaben, propylparaben as well as sodium methylparaben and sodium propylparaben.

The addition of antioxidants is particularly preferable in certain topical applications. Suitable examples therefor are sodium metabisulfite, alpha-tocopherol, ascorbic acid, maleic acid, sodium ascorbate, ascorbyl palmitate, butylated hydroxyanisol, butylated hydroxytoluol, fumaric acid or propyl gallate. Preferred is the use of sodium metabisulfite.

Suitable pH regulators for topical dosage forms are eligible e.g. sodium hydroxide, hydrochloric acid, buffer substances such as sodium dihydrogen phosphate or disodium hydrogenphosphate.

Cream preparations may also contain other excipients and additives, such as fatiquors, solvents, consistency enhancers or hydrotopes for improving the flow characteristics. Herein single as well as several substances from the same group of additives or excipients may be present in the mixture.

Suitable fatiquors are e.g. oleic acid decylester, hydrated castor oil, light mineral oil, mineral oil, polyethylene glycol, sodium laurylsulfate.

Eligible solvents are corn oil, cottonseed oil, peanut oil, sesame oil, soybean oil, ethyl oleate, glycerin, isopropyl myristate, isopropyl palmitate, polyethylene glycol or polypropylene glycol.

Suitable consistency enhancers are e.g. cetyl alcohol, cetyl ester wax, hydrated castor oil, microcrystalline waxes, non-ionic emulsifier waxes, beeswax, paraffin or stearyl alcohol.

Suitable hydrotopes are alcohols such as ethanol, isopropyl alcohol or polyols such as glycerin.

Preparations according to the invention may further contain additives. They are preferably selected from aromatic and flavoring substances, in particular essential oils, vitamins as well as galenics excipients selected from sugars, sugar substitutes, nutritional sweeteners, acidifiers, solubilizers such as water, glycol, glycerin, thickening agents, sweeteners, colorants or preservatives or combinations thereof, also depending from the galenical dosage form.

Suitable aromatic and flavoring substances comprise above all essential oil that can be used for this purpose. In general, this term refers to volatile extracts from plants or parts of plants with the respective characteristic smell. They can be extracted from plants or parts of plants by steam distillation.

Examples to be mentioned are: Essential oils, respectively aromatic substances from sage, cloves, chamomile, anise, star anise, thyme, tea tree, peppermint, mint oil (menthol, cineol), eucalyptus oil, mango, figs, lavender oil, chamomile blossoms, pine needles, cypress, oranges, rosewood, plum, currant, cherry, birch leaves, cinnamon, limes, oranges, grapefruit, tangerine, juniper, valerian, lemon balm, lemon grass, palmarosa, cranberry, pomegranate, rosemary, ginger, pineapple, guava, echinacea, ivy leave extract, blueberry, kaki, melons etc. or mixtures thereof, as well as mixtures of menthol, peppermint and star anise oil or menthol and cherry flavor.

These aromatic or flavoring substances can be included in the range of 0.0001 to 10% per weight (particularly in a composition), preferred 0.001 to 6% per weight, more preferred 0.001 to 4% per weight, most preferred 0.01 to 1% per weight, with regard to the total composition. Application- or single case-related it may be advantageous to use differing quantities.

Thus the compounds according to the invention as well as the aforementioned combinations of active agents are suitable for use for the production of a formulation for oral administration.

Likewise, the compounds according to the invention as well as the aforementioned combinations of active agents are suitable for use for the production of a formulation as lyophilisate or as a liquid formulation.

According to the invention is also the use of compounds according to the invention as well as the aforementioned combinations of active agents for the production of a topical formulation.

The present application refers also to a pharmaceutical composition containing at least one compound according to the invention, or to one of the aforementioned combinations of active agents containing at least one pharmaceutically acceptable carrier, excipient, diluent, cryoprotectant and/or lypoprotectant.

It is preferred when said pharmaceutical composition is suitable for oral, parenteral, topical administration and/or administration by inhalation.

It is also preferred that said pharmaceutical composition is suitable for treatment and/or prophylaxis of retroviral infections and/or their sequelae. It is particularly preferred that said pharmaceutical composition for treatment and/or prophylaxis of retroviral infections and/or their sequelae contains PR-619 as active agent.

The formulations and pharmaceutical compositions described before may contain besides the compounds according to the invention also at least one additional active agent. Suitable as a combinational active agent are the aforementioned active agents for a combinational therapy. It is preferred that the compound according to the invention in said combination formulation or combination composition is PR-619.

The present application refers also to a method of treatment and/or prophylaxis of retroviral infections and/or their sequelae in a human or a vertebrate comprising the administration of a pharmaceutically effective amount of a compound according to general formula (I) or one of its salts and/or solvates and/or hydrates that is suitable to be beneficial for said retroviral infection and/or its sequelae.

It is preferred that the retroviral infections and/or their sequelae of the method of treatment described before is HIV-1 infection, HIV-2 infection, AIDS, AIDS sequelae, FIV infection and SIV infection.

It is also preferred that in the method of treatment described before the at least one active agent according to the invention is administered together with at least one further active agent, wherein said further active agent is selected from a group comprising proteasome inhibitors, reverse transcriptase inhibitors, integrase inhibitors, protease inhibitors, entry inhibitors, HIV vaccine, virostatic agents and immunostimulatory agents, and the combination of active agents is suitable to be beneficial in said retroviral infections and/or its sequelae.

In this combined method of treatment the combination of active agents can be administered separately, or in a joint formulation or composition.

It is particularly preferred that the compound according to the invention in the aforementioned methods of treatment is PR-619.

Furthermore, it is preferred that the inventive combination of active agents in the methods of treatment described before comprises PR-619 and bortezomib or PR-957.

EXAMPLES

Example 1: Inhibition of the Processing of HIV-1 Gag Structure Proteins

In order to investigate whether PR-619 and its derivatives inhibit the processing of HIV-1 Gag structure proteins, Western Blot (WB) analyses were carried out. Therefore, HeLa cell cultures were transfected with the pNLΔenv plasmid which encodes for HIV-1 proteins excluding the env envelope proteins. This enables the production of virus-like particles (VLPs), an established in vitro model in HIV-1 research. 24 h after transfection the cells were transferred to reaction vessels, and a pre-incubation with PR-619 for 1 h was performed. Thereupon, the cells were washed three times with PBS and incubated for 4 h in fresh RPMI medium either with 20 µM PR-619 (Merck-Millipore) or with the corresponding amount of DMSO as solvent control at 37° C.

Then a separation into a cell and a VLP fraction was effected by means of centrifugation. VLPs were purified from the cell culture supernatants via a 20% sucrose cushion. Cells were then washed with PBS and lysed with RIPA buffer. Protein concentrations were determined by means of Bradford protein assays and assimilated for the respective lysates. The cytosolic fraction of cell lysates was denaturized in SDS sample buffer, separated by SDS gel electrophoresis and transferred to a nitrocellulose membrane. Gag proteins were visualized with a Gag-specific antibody (AB) and a horseradish peroxidase-coupled secondary reagent by means of an electrochemiluminescence reaction.

Figure 2:
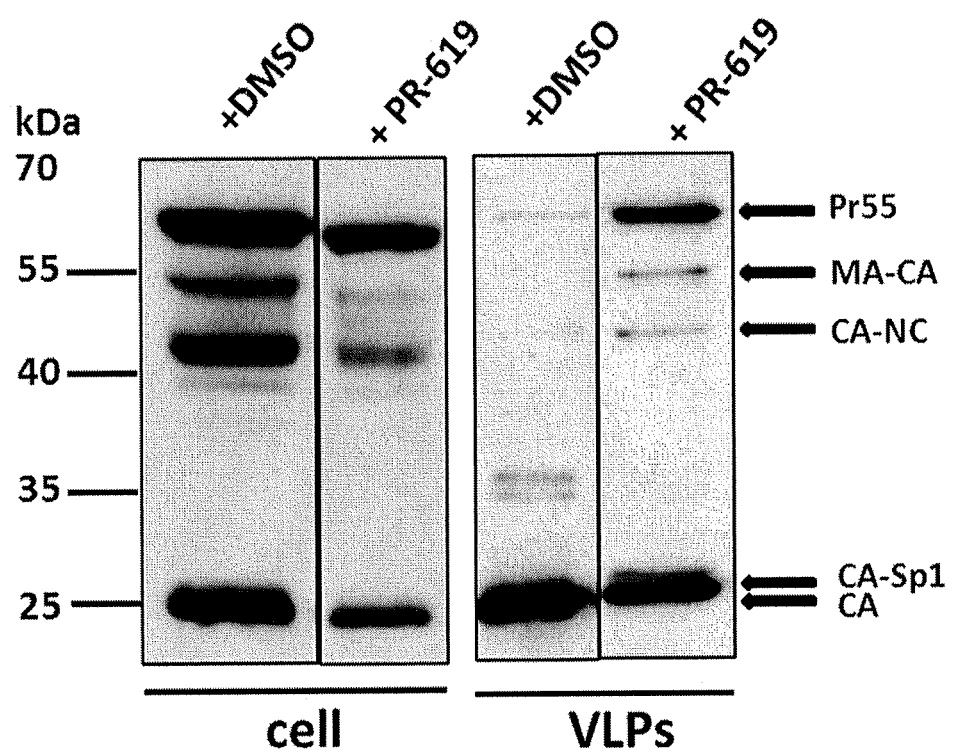

WB results showed that PR-619 significantly inhibits Gag processing. The observed processing defect influences several steps in the maturation of Gag polyprotein Pr55. The complete cleavage of HIV-1 Pr55 leads in general to the generation of mature Gag proteins MA, CA, NC and p6Gag, as well as two minor spacer peptides (SP2 and SP1) that link the respective domains (FIG. 1). Several of these cleavage processes are inhibited in the process of Gag processing through the interaction with PR-619, since the presence of intermediates of Gag processing such as MA-CA (p41), p39 (CA-NC) or CA—the 14 amino acid long SP1 (p25CA) after blocking proteasome activity was observed (FIG. 2).

A densitometric evaluation of Gag processing in the VLP fraction was carried out with the analysis program AIDA®. The densitometric evaluation allows for the quantification of signal intensities in Western Blot and thus conclusions on the quantity of a certain protein in the sample. Herein, the intensity strength of CA is set into relation with the sum of intensity strengths of the total Gag content, and thus the percentage of CA in the VLPs is indicated.

Figure 3:
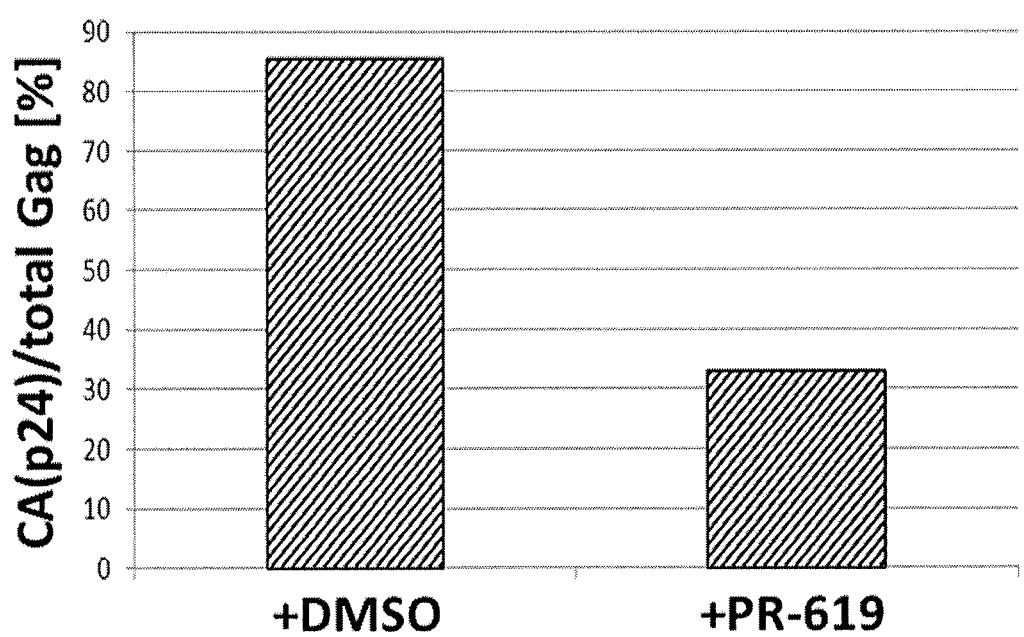

The evaluation showed clearly that after addition of PR-619 the generation of the main Gag processing product CA which is a marker for infectious HIV-1 virions is clearly inhibited (FIG. 3).

Taken together, it is stated that PR-619 interferes with the proteolytic maturation of Gag proteins and that the generation of the main Gag processing product CA is inhibited.

Example 2: The DUB Inhibitor PR-619 Inhibits HIV-1 Replication in a Concentration-Dependent Manner in Primary T Cells and Macrophages without Influencing the Vitality of the Host Cell As could be shown in the preceding example that PR-619 inhibits the late processes in Gag processing this effect on the spread of infection was investigated. According to the invention, isolated primary human peripheral blood mononuclear cell (PBMC) cultures were infected to this aim with the virus strain HIV-1$_{NL4-3}$(X4 tropic) or HIV-1 NL$_{NL4-3}$(R5 tropic). One day after infection cells were washed with PBS (phosphate buffer saline), provided with fresh medium containing the DUB inhibitor PR-619 in several non-cytotoxic concentrations (3.5 µM, 7 µM, 14 µM, 28 µM). The treatment with DUB inhibitors was carried out over the entire experimental period ("permanent treatment") or only on Day 1 and Day 3 after infection ("structured treatment"). In the infection with HIV-1$_{NL4-3}$ (R5 tropic), only a permanent treatment was performed. Each 2-3 days samples from the cell culture supernatants were taken, frozen and later on used for determining reverse transcriptase activity. Concomitantly, 80% of the cell culture medium was replaced and fresh PR-619 was added. Reverse transcriptase activity (ccpm) was determined in the cell-free cell culture supernatants and plotted against time (FIGS. 4A and 4B; the black arrows indicate the treatment with PR-619).

Herein, a dose-dependent inhibition of HIV-1 replication was shown in T cells. Already with a concentration of 3.5 µM the DUB inhibitor PR-619 showed a clear (in structured treatment) or complete (in permanent treatment) inhibition of the HIV-1 replication (FIGS. 4A and 4B). Interestingly, HIV-1 starts to replicate again one week after termination of the structured treatment with 3.5 µM PR-619 (FIG. 4A). This shows that the observed antiretroviral effects are not due to an unspecific cytotoxic effect of PR-619. This observation underscores the specific effect of DUB inhibitors on HIV-1 replication.

For six different donors the area under the curve (AUC) in the HIV-1 replication profiles after infection of PBMCs with T-cell tropic virus was determined, representing the HIV-1 replication capacity.

The evaluation of 6 replication profiles showed in structured as well as in permanent treatment with PR-619 a significant dose-dependent reduction of the HIV-1 replication capacity in T cells. Using a concentration of 3.5 µM PR-619 a reduction of the replication capacity by 23% (±14%) was observed in structured treatment, using 7 µM by 94%(±14%) and using 14 µM by 100%. In permanent treatment 3.5 µM yielded a reduction by 50%(±16%), 7 µM a reduction by 97%(±15%) and 14 µM by 100%.

For verifying whether after adding PR-619 the replication is also inhibited in macrophages, a potential reservoir for HIV-1, the replication profiles of 5 donors after infection with macrophage-tropic virus were evaluated. It showed that also in macrophages the treatment with PR-619 leads dose-dependently to a significant reduction of the HIV-1 replication capacity. In permanent treatment 3.5 µM yielded a reduction by 35%(±8%), 7 µM a reduction by 60%(±9%) and 14 µM by 100%.

Taken together, it can be stated that the inventive use of PR-619 leads dose-dependently in structured as well as in permanent treatment to a complete inhibition of HIV-1 replication in T cells and in macrophages.

Example 3: Comparison of the Effect of PR-619 with DUB Inhibitors P005091, WP1130 and P22077

For comparative purposes, the anti-retroviral effect found for PR-619 was compared with three other DUB inhibitors P005091, WP1130 and P22077. Experiments were carried out as described in Example 2.

Figure 5:
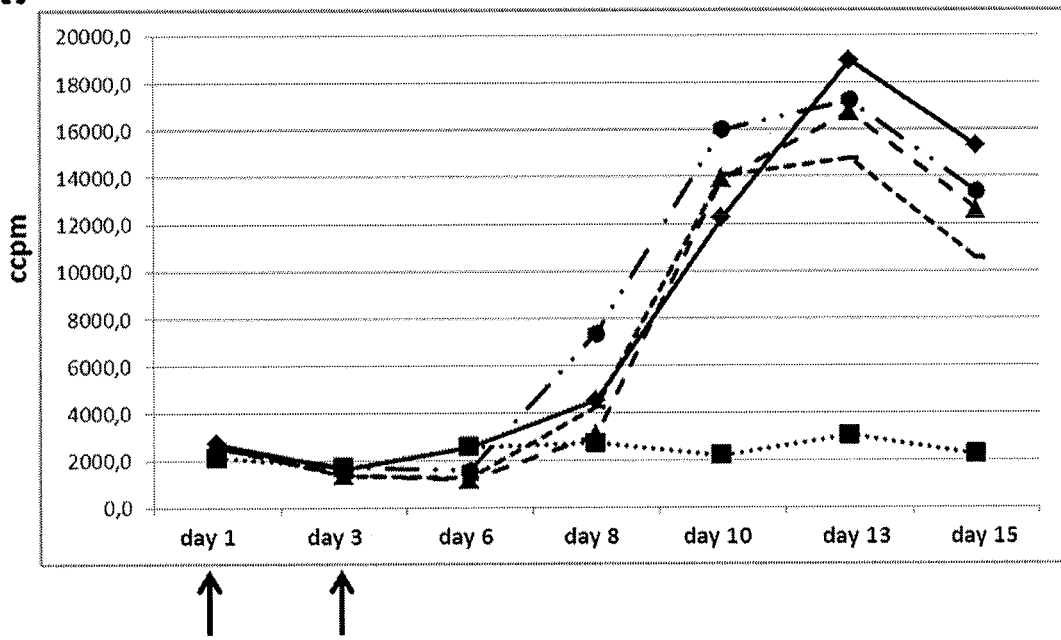
Figure 5:
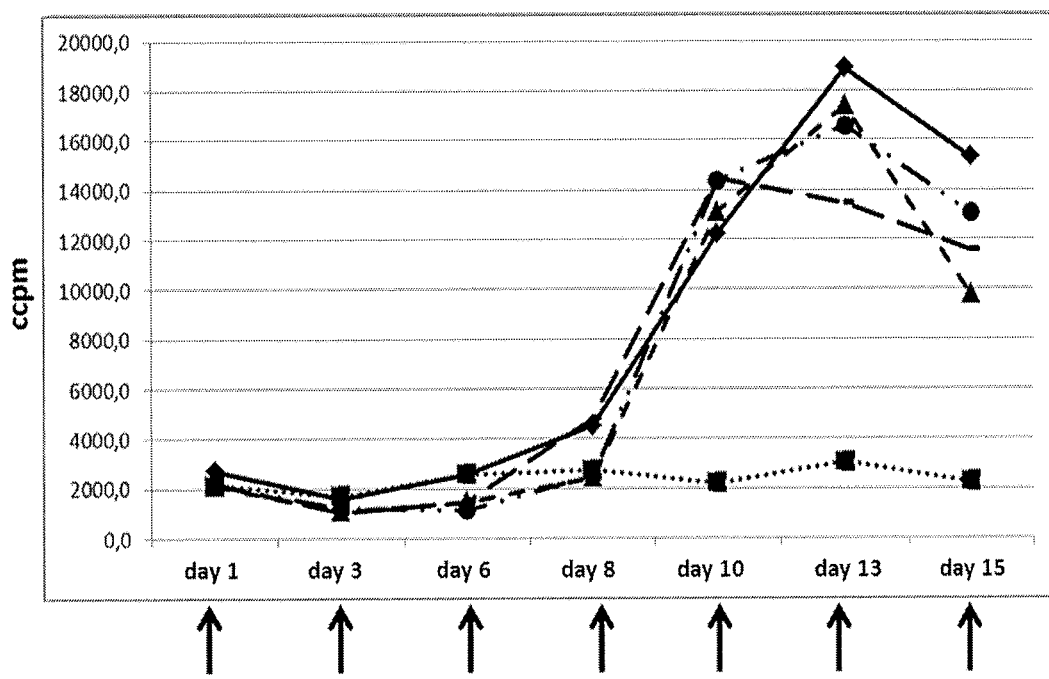

It showed that the DUB inhibitor P005091 (Tocris) which highly specifically inhibits USP7 does not inhibit HIV-1 replication neither in T cells nor in macrophages in the applied non-cytotoxic concentrations of 0.75 µM, 1.5 µM and 3 µM (FIGS. 5A and 5B). The statistic evaluation of 5 replication profiles shows neither for the structured nor for the permanent treatment of T cells and macrophages a significant reduction of the HIV-1 replication. In all cases the replication capacity is in the range of the untreated control.

Figure 6:
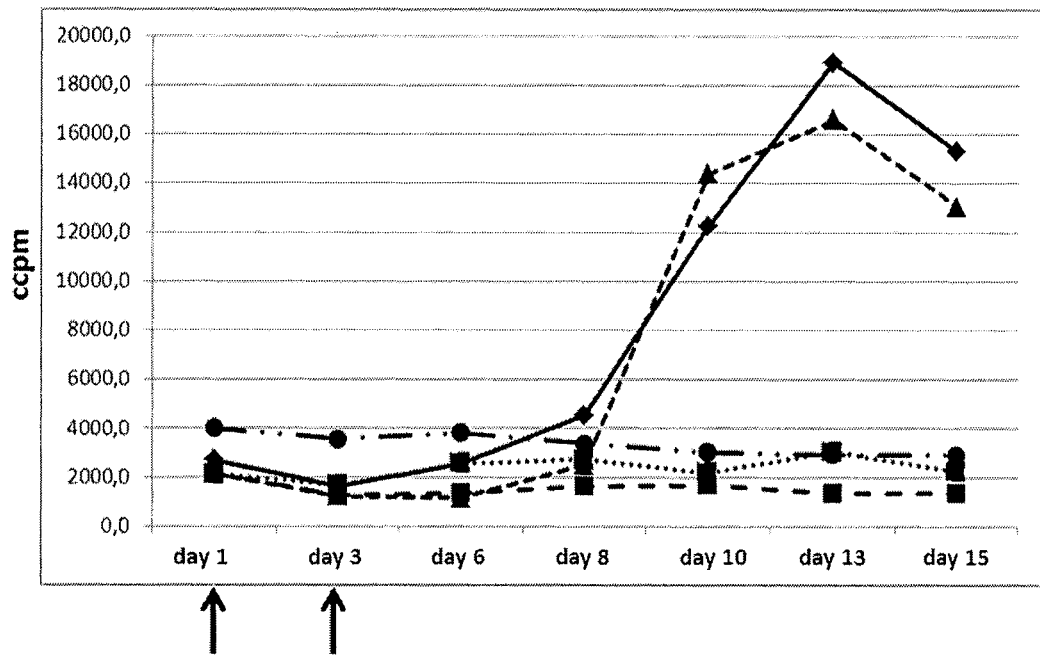
Figure 6:
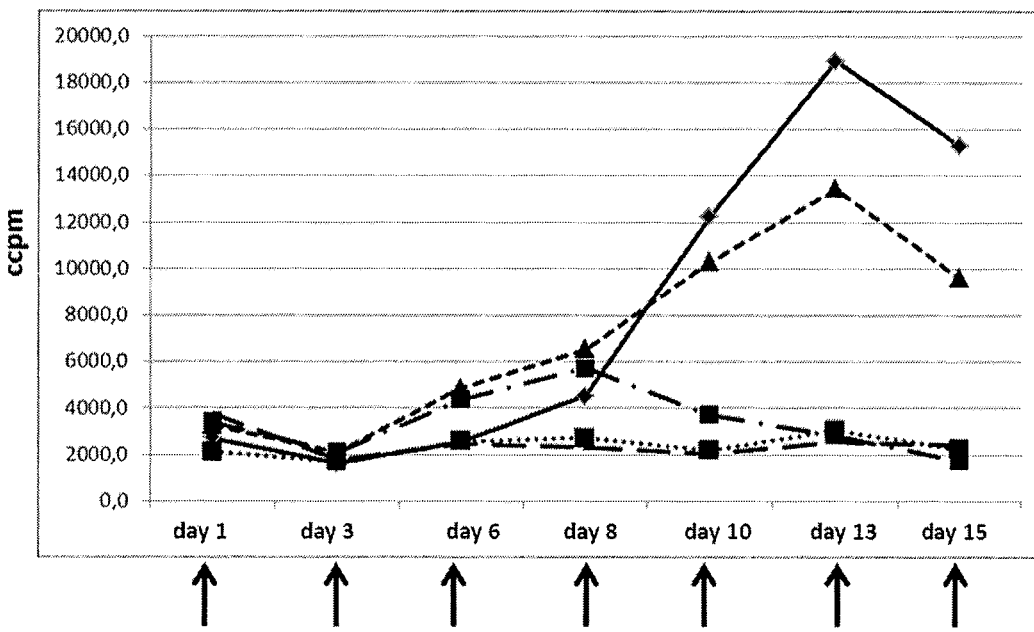

Neither the treatment of PBMCs with the DUB inhibitor WP1130 (Merck Millipore) in the applied non-cytotoxic doses of 3 µM and 6 µM showed an influence of HIV-1 replication in T cells and macrophages (FIGS. 6A and 6B). The slight reduction of the replication capacity during permanent treatment (FIG. 6B) with 3 µM WP1130 could be explained with an already appearing toxicity (cf. FIGS. 10A and 10B). The loss in replication capacity with higher concentrations of WP1130 is due to the high toxicity in this concentration range (FIGS. 10A and 10B). Also using WP1130 the statistic evaluation of 5 replication profiles showed for the structured as well as for the permanent treatment no significant reduction of the HIV-1 replication neither in T cells nor in macrophages. In all cases the replication capacity is in the range of the untreated control.

The treatment with the DUB inhibitor P22077 in non-cytotoxic concentrations of 7.5 µM, 15 µM, 30 µM and 60 µM showed as with PR-619 a nearly complete inhibition of HIV replication. A general cytotoxic damage of the host cell does not exist. This observation underlines the specific effect of DUB inhibitors on HIV-1 replication.

Taken together, it can be concluded from Examples 2 and 3 that the DUB inhibitor PR-619 inhibits highly specifically the HIV-1 replication and that this inhibition can obviously not be reached with all DUB inhibitors.

From the specific inhibition profiles of the applied DUB inhibitors P22077, PR-619, P005091 and WP1130 (see above) it can be concluded that the common mechanism of action must be an inhibition of the enzyme USP47. This is the only DUB protein that can be inhibited by P22077 as well as by PR-619, but not by P005091 and WP1130. Therefore, it can be concluded that USP47 is essential for the HIV-1 replication.

Example 4: Experiments on the Cytotoxicity of PR-619, P005091 and WP1130

For addressing the question whether PR-619 triggers a cytotoxic effect in the abovementioned systems non-infected PBMC cultures were treated in parallel to the replication studies with the same concentrations of PR-619. Toxicity was assessed with a WST assay. Herein viable cells with an intact mitochondrial succinate-tetrazolium dehydrogenase system effect an enzymatic conversion of the feebly red tetrazolium salt WST-1 (4-[3-(4-iodophenyl)-2-(4-nitrophenyl)-2H-5tetrazolio]-1,3 benzene disulfonate) into the dark red formazan. This color change can be measured photometrically in a spectrophotometer. Thus, the WST assay is a very sensitive method for measuring the toxicity of substances on the cell metabolism.

Figure 8:
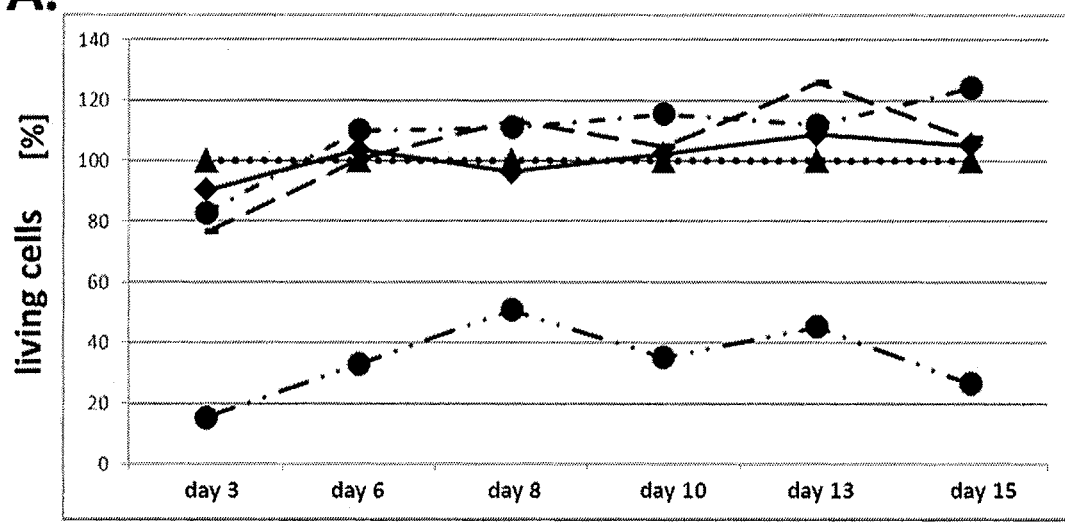
Figure 8:
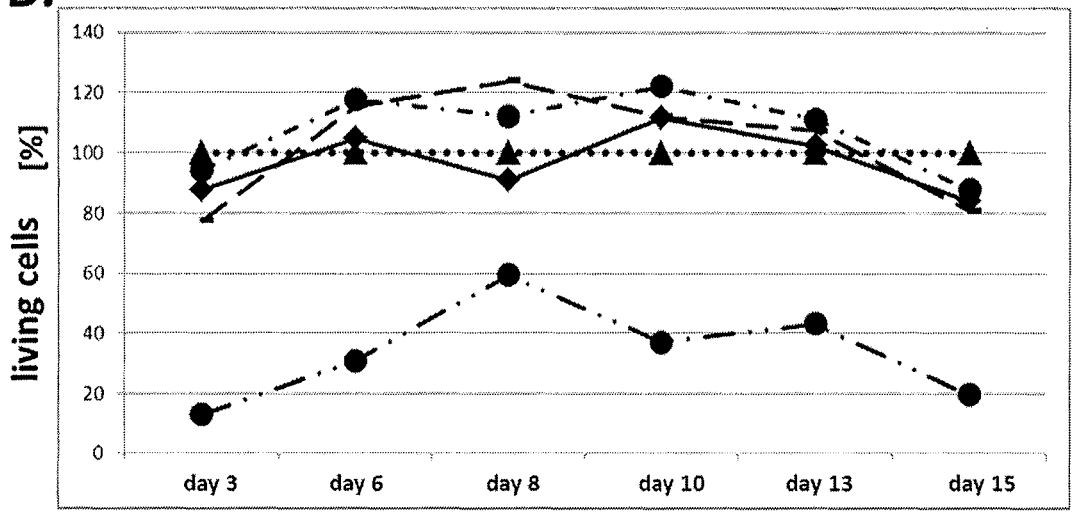

In FIGS. 8A ("structured treatment") and 8B ("permanent treatment") the percentage of dead cells is depicted, respectively, in comparison to untreated cells (the value for untreated cells was set to 100%, respectively).

It showed that PR-619 did not display any significant toxic effect in antivirally effective concentrations during an observation period of 15 days. Using PR-619 only a clear toxic effect starts using a concentration of 28 µM (in contrast, the antiviral efficacy is already about 3.5 µM).

Thus, it can be stated that the antiviral effect of PR-619 is not due to unspecific cytotoxic effects.

Comparative experiments were performed with P005091 and WP1130. To this aim, the toxicity of these two DUB inhibitors was determined after treatment of PBMC cells on day 13 by means of the WST assay. The respective percentage of dead cells was depicted in comparison to untreated control (100%).

Herein, it showed that the DUB inhibitor P005091 shows no toxicity in the applied concentrations of 0.75-3 µM (FIGS. 9A and 9B). After treatment with the DUB inhibitor WP1130 a reduction in living cells by 40% occurred during permanent treatment already with the lowest applied concentration of 3 µM. A concentration >3 µM led to a complete death of the cells (FIGS. 10A and 10B).

Example 5: PR-619 Increases Dose-Dependently the MHC-I Antigen Presentation of Viral Structural Proteins From Applicant's previous investigations it is known that the polyubiquitination of Gag leads to an enhanced entry into the UPS and as a consequence to an enhanced MHC-I antigen presentation. In order to investigate whether the use according to the invention of PR-619 augments the MHC-I antigen presentation and thus the immunogenicity of HIV-1 Gag proteins in regard of the CD8$^+$ T cell response the MHC-I antigen presentation of Gag-derived epitopes was determined.

Since there is no conformation-dependent MHC-I specific antibody that could detect Gag epitopes bound to human MHC-I molecules the ovalbumin-derived sequence SIINFEKL (SL) was introduced as a model epitope into the non-structured SP1 spacer region of Gag. For measuring the MHC-I antigen presentation, HeLa cells constitutively expressing the murine SL-binding MHC-I allotype H2-$K_b$ (HeLa-$K_b$) (Porgador et al., 1997, Immunity 6(6), 715-726) were transfected with expression plasmids coding for Gag-SL proteins. Performing flow cytometric analyses the monoclonal antibody (mAB) 25D1.16 was used which recognizes specifically SL in the complex with H2-$K_b$.

24 h after transfection the cells were incubated overnight with different concentrations of the DUB inhibitor PR-619 (7 and 14 µM).

Then, an acid wash (acid washing buffer pH 3) was carried out for removing the H2-$K_b$-SL complexes from the cell surface. Thereafter, the cells were incubated with and without PR-619 for 4 h at 37° C. and then the newly loaded H2-$K_b$-SL complexes at the cell surface under inhibition with PR-619 were determined by FACS analysis with the monoclonal AB 25D1.16. For compensating possible differences in the expression level of Gag-SL, the mean fluorescence intensity (MFI) of the 25D1.16 staining was normalized to the MFI of the intracellular Gag signal.

Figure 11:
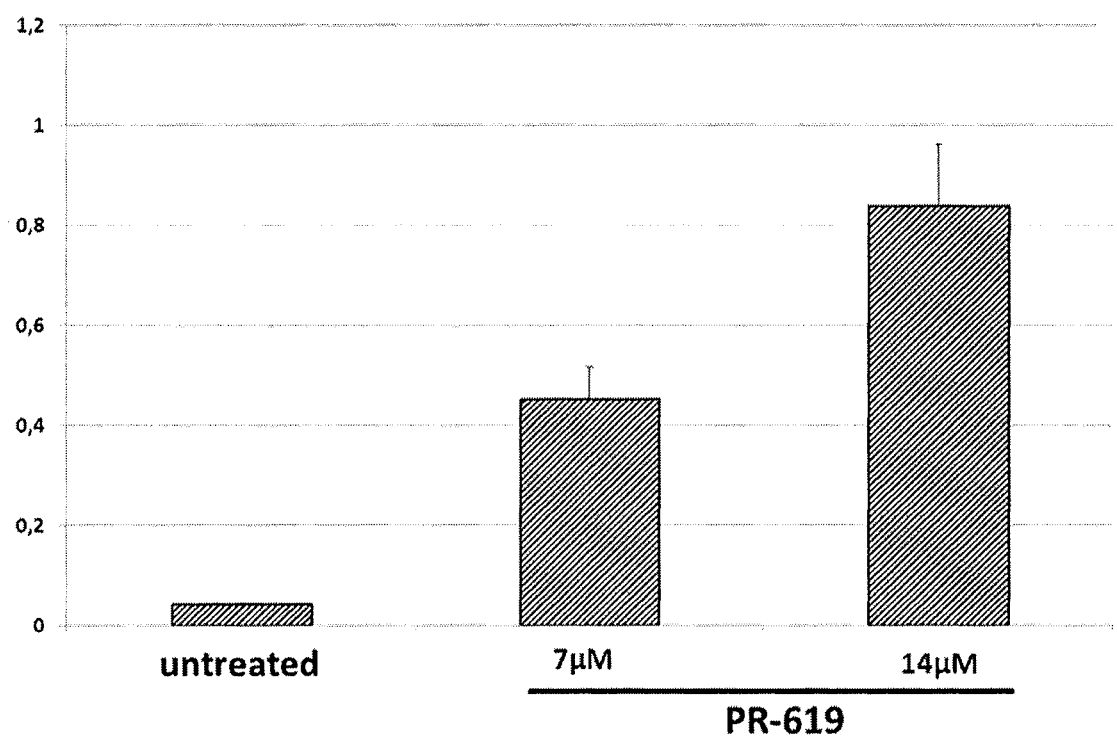

Herein, it can be clearly seen that the treatment of the cells with PR-619 increases dose-dependently the MHC-I antigen presentation of Gag-derived epitopes 6-fold (FIG. 11).

Taken together, it can be stated that the use of PR-619 according to the invention does not only inhibit the HIV-1 replication but concomitantly enhances the immunogenicity of HIV-1 structural proteins in a considerable manner.

Example 6: The DUB Inhibitor PR-619 in Combination with the Proteasome Inhibitor Bortezomib Inhibits the HIV-1 Replication Synergistically in T Cells and Macrophages In order to clarify the question whether a combined permanent treatment with PR-619 and the proteasome inhibitor bortezomib (Velcade®) causes a synergistic effect on the replication capacity of HIV-1, a cross titration was carried out with both substances (analogous to Example 2 and 3). Herein, PBMC cultures were treated permanently after infection with the virus strain HIV-1$_{NL4-3}$, first only with the DUB inhibitor PR-619 or with the proteasome inhibitor bortezomib in non-toxic increasing concentrations (PR-619: 0.3 µM, 0.9 µM, 2.75 µM and 8 µM; bortezomib: 0.6 nM, 1.5 nM, 5.3 nM and 16 nM).

In a further set of experiments, a cross titration with PR-619 and bortezomib was performed. Herein, the cells were treated permanently with constantly 0.6 nM bortezomib and increasing concentrations of PR-619 (0.3 µM, 0.9 µM, 2.7 µM and 8 µM). Experiments were carried out as described in Example 2. It showed that the proteasome inhibitor bortezomib inhibits the HIV-1 replication in T cells as well as in macrophages beginning with a concentration of 5.3 nM. FIG. 12A shows the result in T cells. The DUB inhibitor PR-619 is able to inhibit the HIV-1 replication beginning with a concentration of 2.7 µM (FIG. 12B).

After treatment of the PBMC cultures with a constant concentration of 0.6 nM bortezomib and increasing concentrations of PR-619 (0.3 µM, 0.9 µM, 2.7 µM and 8 µM) already the lowest concentrations used, 0.3 µM PR-619 and 9.6 nM bortezomib, showed a complete inhibition of the replication. This could be observed in T cells (FIG. 12C) as well as in macrophages. In these low concentrations the substances, when applied alone, were not able to reduce the HIV-1 replication capacity.

The statistic evaluation of the HIV-1 replication capacity after infection of PBMC from 4 different donors yielded that the combined use of constantly 0.6 nM bortezomib and 0.3 µM PR-619 inhibited the HIV-1 replication by 55%(±13%), 0.9 µM PR-619 by approx. 72%(±9%) and 2.7 µM PR-619 by 90%(±4%).

After infection of macrophages from 5 different donors the statistic evaluation of the HIV-1 replication capacity yielded that the combined use of constantly 0.6 nM bortezomib and 0.3 µM PR-619 inhibited the HIV-1 replication by 45%(±14%), 0.9 µM PR-619 by approx. 73%(±9%) and 2.7 µM PR-619 by 87%(±4%).

According to the invention these results show that the combined use of PR-619 and bortezomib in very low concentrations, respectively, displays a supra-additive synergistic inhibition of the HIV-1 replication in T cells and macrophages.

Figure 13:
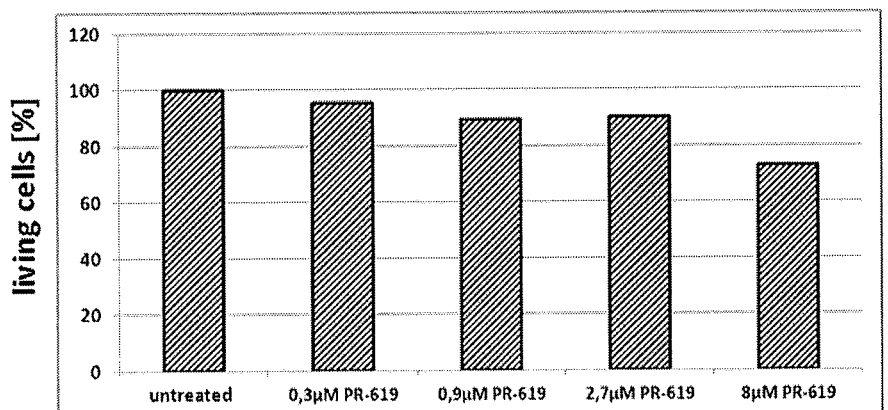
Figure 13:
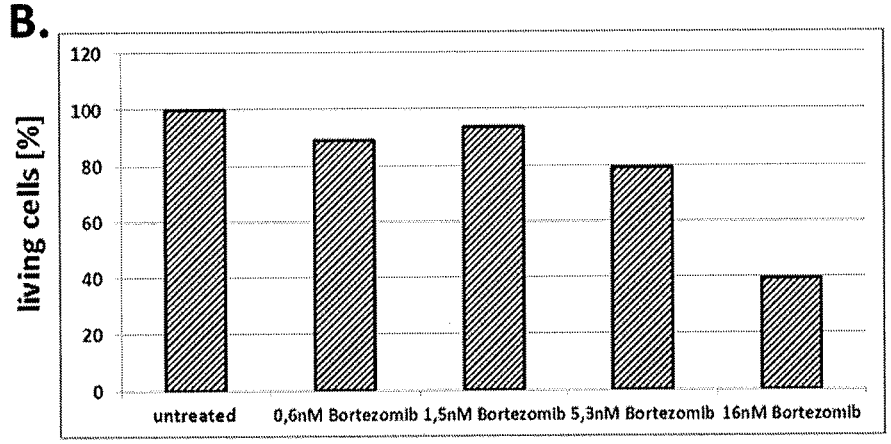
Figure 13:
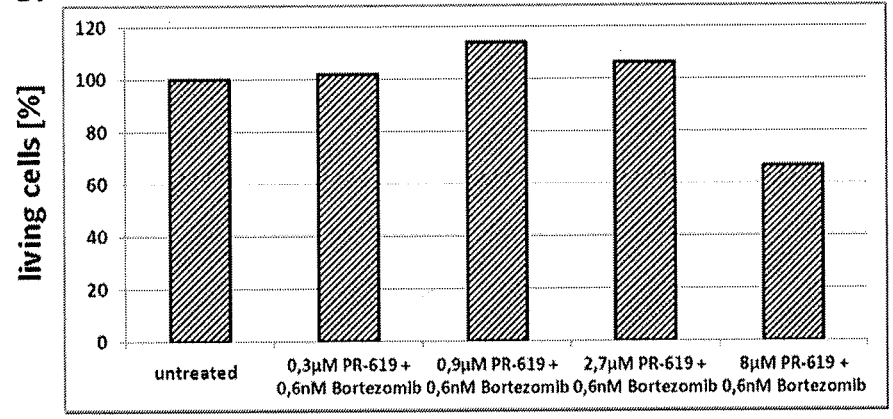

Example 7: Studies on the Cytotoxicity of PR-619, Bortezomib and of the Combination of Both Substances in Permanent Treatment To clarify the question whether PR-619 or bortezomib used alone or in a combined treatment trigger cytotoxic effects in said systems, non-infected PBMC cultures were treated in parallel to the replication studies (described in Example 2) with the same concentrations of PR-619, bortezomib and of the combination of both substances. The toxicity was assessed performing a WST-assay, as described in Example 4. FIG. 13 depicts the respective percentage of dead cells in comparison to untreated cells (the value of the untreated cells was set as 100%, respectively).

It showed that PR-619 in antiretrovirally effective concentrations does not display a significant toxic effect during the observation period of 15 days. PR-619 did not show either a clear toxic effect with highest used concentration of 8 µM (FIG. 13A).

Comparative experiments were performed with the proteasome inhibitor bortezomib. Herein, it was shown that bortezomib did not display any toxicity in the concentration range of 0.6-5.3 nM (FIG. 13B). Starting with a concentration of 16 nM a reduction in living cells by 60% was detected.

The combination of both substances did not display any toxicity in the antiretrovirally effective concentrations of 0.6 nM bortezomib+0.3 µM, 0.9 µM, 2.7 µM PR-619 (FIG. 13C). Only with a concentration of 8 µM PR-619 and 0.6 nM bortezomib a reduction of the living cells by 40% was observed.

Thus, it can be stated that the antiretroviral effect of the combined treatment with PR-619 and bortezomib is not caused by unspecific cytotoxic effects but is due to a specific synergistic mechanism of action.

Example 8: The DUB Inhibitor PR-619 in Combination with the Proteasome Inhibitor PR-957 Inhibits Dose-Dependently the HIV-1 Replication in the HLAC System In order to address the question whether a combined permanent treatment also shows a synergistic effect on the inhibition of the replication capacity of HIV-1 with another highly specific proteasome inhibitor, the specific immunoproteasome inhibitor PR-957 was used that—in contrast to bortezomib—belongs to the group of epoxyketones. A cross titration with both substances was performed (analogous to Example 6). Herein PBMC cultures were permanently treated after infection with the viral strain HIV-1$_{NL4-3}$ X4-tropic first only with the DUB inhibitor PR-619 or with the immunoproteasome inhibitor PR-957 in non-toxic increasing concentrations (PR-619: 0.3 µM, 0.9 µM, 2.7 µM and 8 µM; PR-957: 20 nM, 40 nM, 80 nM and 160 nM). In a further set of experiments a cross filtration with PR-619 and PR-957 was carried out. Herein, the cells were permanently treated with constantly 40 nM PR-957 and increasing concentrations of PR-619 (0.3 µM, 0.9 µM, 2.7 µM and 8 µM). The experiments were carried out as described in Example 6. It could be shown that the immunoproteasome inhibitor PR-957 inhibits the HIV-1 replication beginning with a concentration of 80 nM (FIG. 14A). The DUB inhibitor PR-619 is able to inhibit the HIV-1 replication beginning with a concentration of 2.7 µM (FIG. 14B). After treatment of the PBMC cultures with a constant concentration of 40 nM PR-957 and increasing concentrations of PR-619 (0.3 µM, 0.9 µM, 2.7 µM and 8 µM) already at 0.9 µM PR-619 and 40 nM PR-957, a complete inhibition of the replication could be detected (FIG. 14C). In these low concentrations the substances were not able, when used alone, to reduce the HIV-1 replication capacity.

The statistic evaluation of the HIV-1 replication capacity after infection of PBMCs yielded that the combined use of constantly 40 nM PR-957 and 0.3 µM PR-619 inhibits the HIV-1 replication by 56%, 0.9 µM PR-619 by 84% and 2.7 µM PR-619 by 94%.

These results show that the combined use of PR-619 and PR-957 in very low concentrations, respectively, effects a supra-additive synergistic inhibition of the HIV-1 replication.

Figure 15:
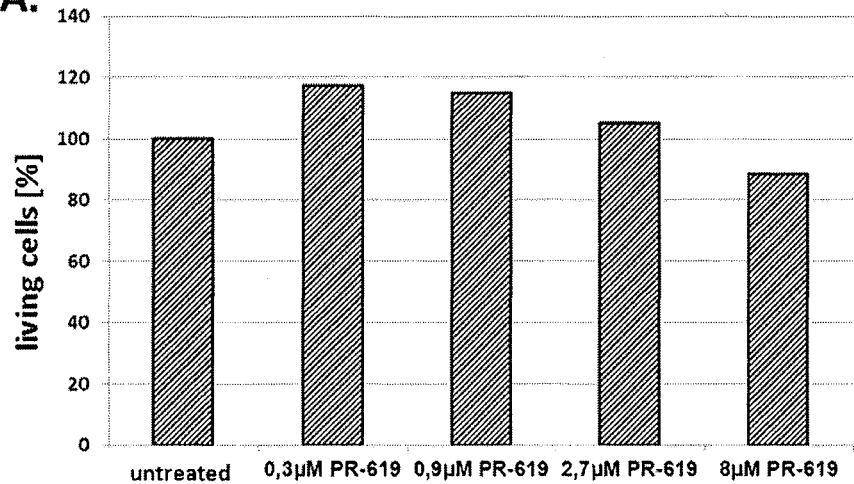
Figure 15:
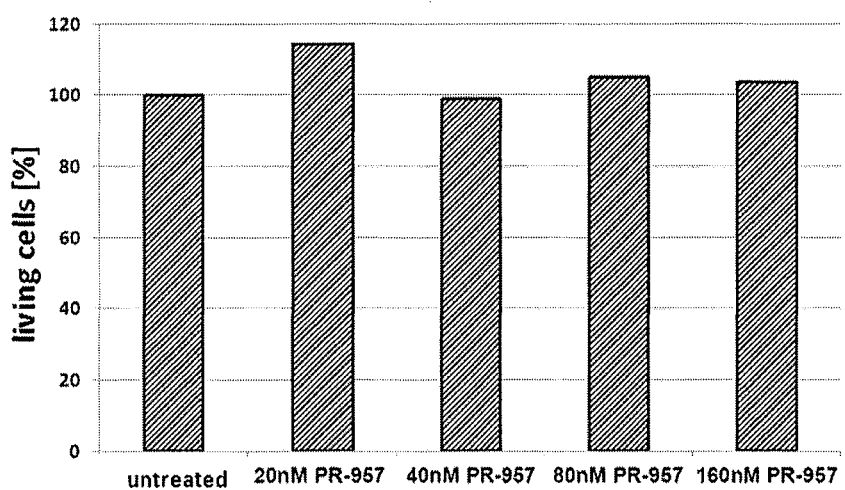
Figure 15:
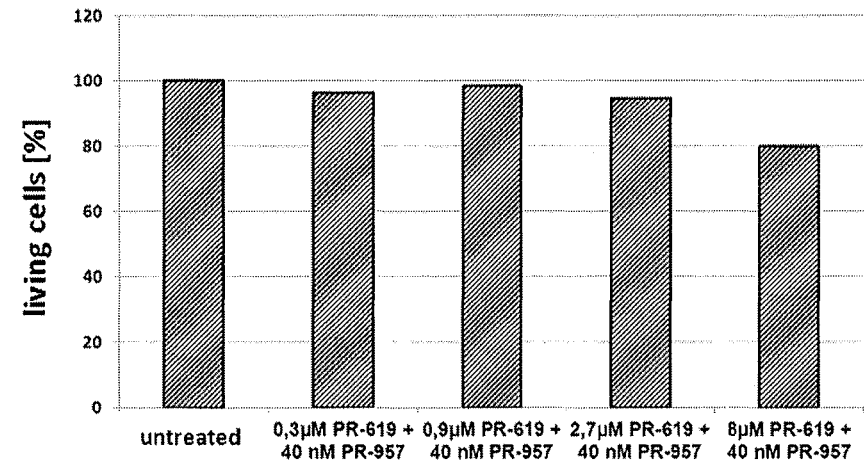

Example 9: Studies on the Cytotoxicity of PR-619, PR-957 and the Combination of Both Substances in Permanent Treatment To clarify the question whether PR-619 or PR-957 used alone or in a combined treatment trigger cytotoxic effects in said systems, non-infected PBMC cultures were treated in parallel to the replication studies (described in Example 8) with the same concentrations of PR-619, PR-957 and of the combination of both substances. The toxicity was assessed by performing a WST-assay, as described in Example 4. FIG. 15 depicts the respective percentage of dead cells in comparison to untreated cells (the value of the untreated cells was set as 100%, respectively).

It showed that PR-619 in antiretrovirally effective concentrations does not display a significant toxic effect during the observation period of 15 days. PR-619 did not show either a clear toxic effect with highest used concentration of 8 µM (FIG. 15A).

Comparative experiments were performed with the immunoproteasome inhibitor PR-957. Herein, it was shown that PR-957 did not display any toxicity in the concentration range of 20-160 nM (FIG. 15B).

The combination of both substances did not display any toxicity in the antiretrovirally effective concentrations (40 nM PR-957+0.3 µM, 0.9 µM, 2.7 µM PR-619 (FIG. 15C). Only using a concentration of 8 µM PR-619 and 40 nM PR-957 a reduction of the living cells by 20% was observed.

Thus, it can be stated that the antiretroviral effect of the combined treatment with PR-619 and PR-957 is not caused by unspecific cytotoxic effects but is due to a specific synergistic mechanism of action.

Example 10: The DUB Inhibitor PR-619 Inhibits Dose-Dependently the HIV-1 Replication in the Human Lymphoid Aggregate Culture (HLAC) Ex Vivo System Without Biasing the Vitality of the Host Cell In order to substantiate the inhibition of the HIV replication under treatment with PR-619, as observed in Example 2, according to the invention human ex vivo cultivated tonsillar tissue was infected with the virus strain HIV-1$_{NL4-3}$ (X4-tropic) or HIV-1$_{NL4-3}$ (R5-tropic). The experiments were carried out as described in Example 2.

A dose-dependent inhibition of the HIV-1 replication in T cells and macrophages using the HLAC system was shown. While 1.25 µM PR-619 did not exert an inhibitory effect on the HIV-1 replication, the use of 2.5 µM, 5 µM and 10 µM PR-619 caused a clear, respectively complete inhibition of the replication.

The statistic evaluation of 3 replication profiles under permanent treatment with PR-619 yielded a significant dose-dependent reduction of the HIV-1 replication capacity in T cells and macrophages. With a concentration of 2.5 µM PR-619 the replication capacity was reduced by 40%(±9%), with 5 µM by 86%(±2%) and with 10 µM completely.

Thus, the use of the DUB inhibitor PR-619 according to the invention leads dose-dependently to a complete inhibition of the HIV-1 replication in the HLAC system.

Example 11: Studies on the Cytotoxicity of PR-619 in Permanent Treatment of Ex Vivo Tonsillar Tissue (HLAC)

To clarify the question whether PR-619 triggers a cytotoxic effect in said systems (Example 10), the infected HLAC cultures from the ex vivo cultivated tonsillar tissue were treated in parallel to the replication studies (described in Example 10) with the same concentrations of PR-619. The toxicity was assessed performing a WST-assay, as described in Example 4.

It was shown that PR-619 did not display any significant toxic effect in all applied antiretrovirally effective concentrations during the observation period of 15 days. Even with the highest concentration of 10 µM PR-619 no toxic effects were observed.

Thus, it can be stated that the antiretroviral effect after treatment of ex vivo HLAC cultures with PR-619 is not caused by unspecific cytotoxic effects but is due to a specific mechanism of action.

FIGURES

FIG. 1: Processing scheme of Pr55Gag

FIG. 2: Western Blots of the Pr55Gag processing products after addition of PR-619

FIG. 3: Densitometric evaluation of the VLP fractions from FIG. 2

Figure 4:
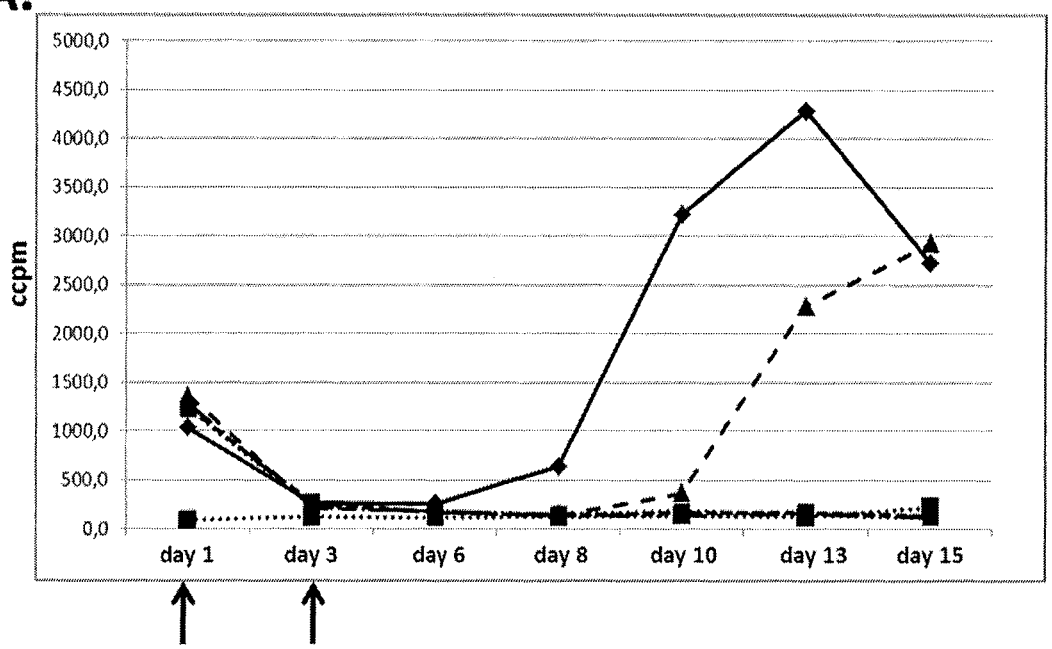
Figure 4:
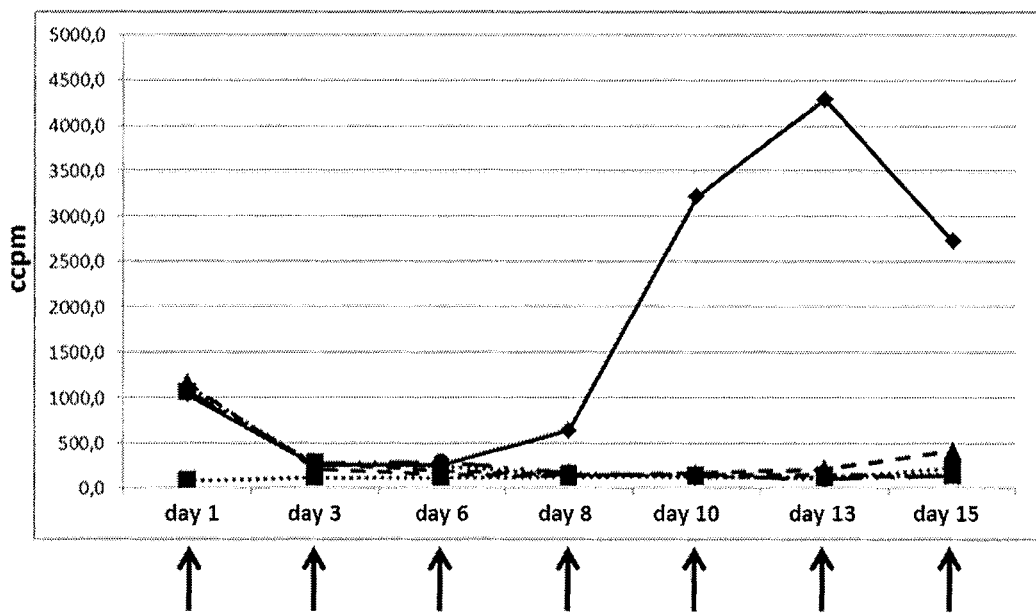
Figure 7:
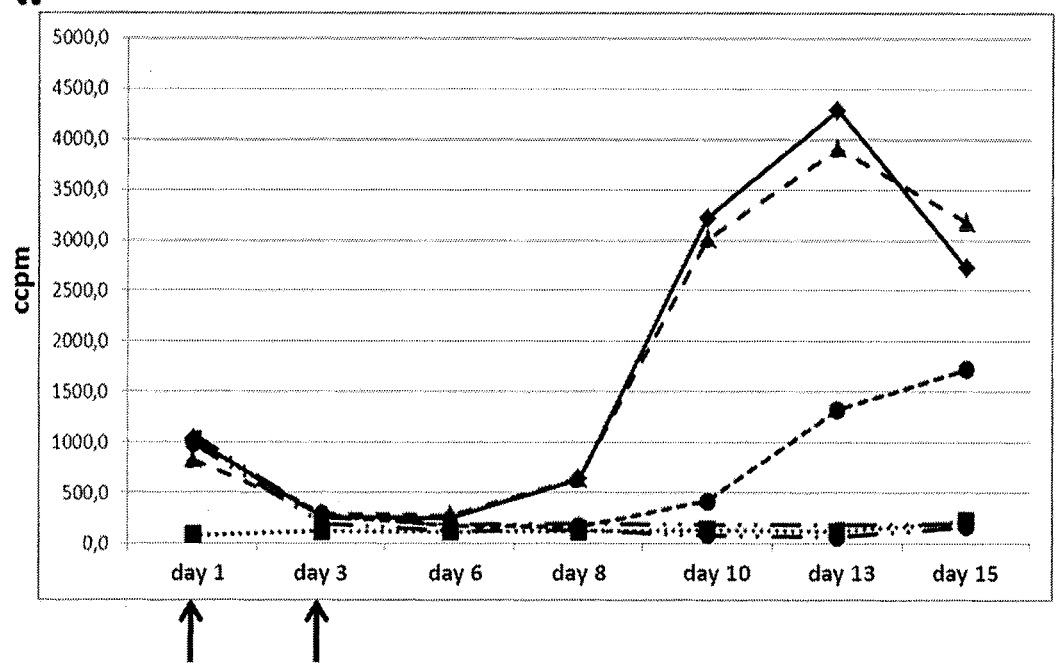
Figure 7:
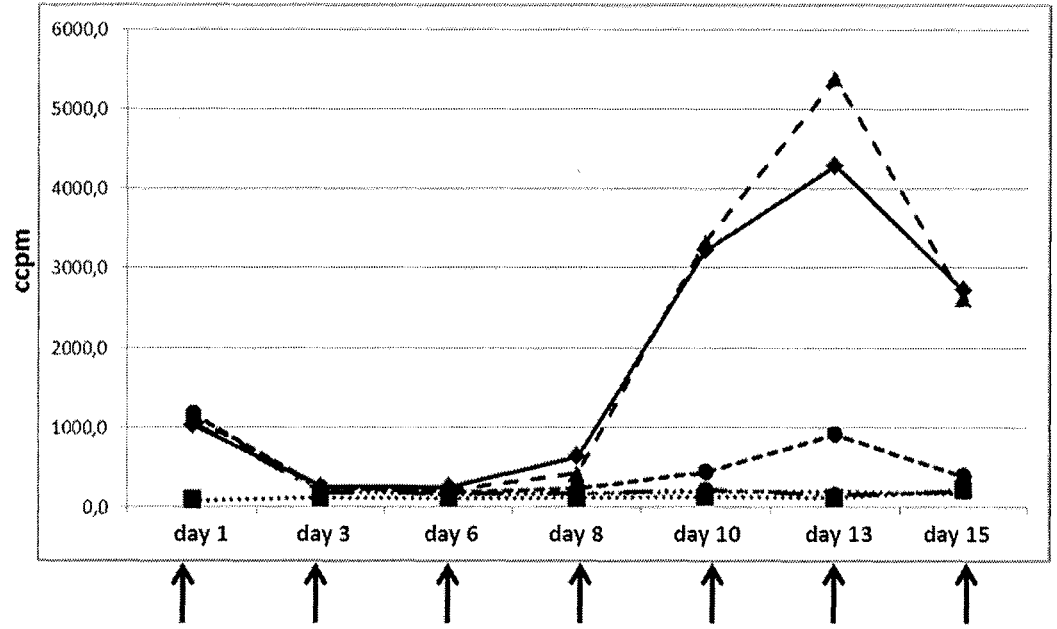

FIG. 4: "Structured treatment" (A) and "Permanent treatment" (B) of HIV-1-infected T cells with different concentrations of PR-619
··■·· not infected ◆ untreated
-▲- $PR\text{-}619^{3.5\ \mu m}$ -●- $PR\text{-}619^{7\ \mu m}$ —*— $PR\text{-}619^{14\ \mu m}$ -●- $PR\text{-}619^{28\ \mu m}$ FIG. 5: "Structured treatment" (A) and "Permanent treatment" (B) of HIV-1-infected T cells with different concentrations of P005091
··■·· not infected ◆ untreated
-▲- $POO\text{-}5091^{0.75\ \mu m}$ —Ω— $POO\text{-}5091^{1.5\ \mu m}$ -●- $POO\text{-}5091^{3\ \mu m}$ FIG. 6: "Structured treatment" (A) and "Permanent treatment" (B) of HIV-1-infected T cells with different concentrations of WP1130
··■·· not infected ◆ untreated
-▲- $WP1130^{3\ \mu m}$ —Ω— $WP1130^{3\ \mu m}$ -●- $WP1130^{3\ \mu m}$ FIG. 7: "Structured treatment" (A) and "Permanent treatment" (B) of HIV-1-infected T cells with different concentrations of P22077
··■·· not infected ◆ untreated
-▲- $P22077^{7.5\ \mu m}$ -●- $P22077^{15\ \mu m}$ —Ω— $P22077^{30\ \mu m}$ -●- $P22077^{60\ \mu m}$ FIG. 8: Percentage of living cells after treatment with different concentrations of PR-619 with "Structured treatment" (A) and "Permanent treatment" (B) over a period of 15 days ‑▲‑ untreated
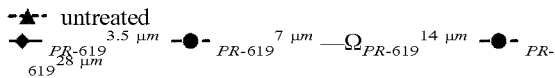

Figure 9:
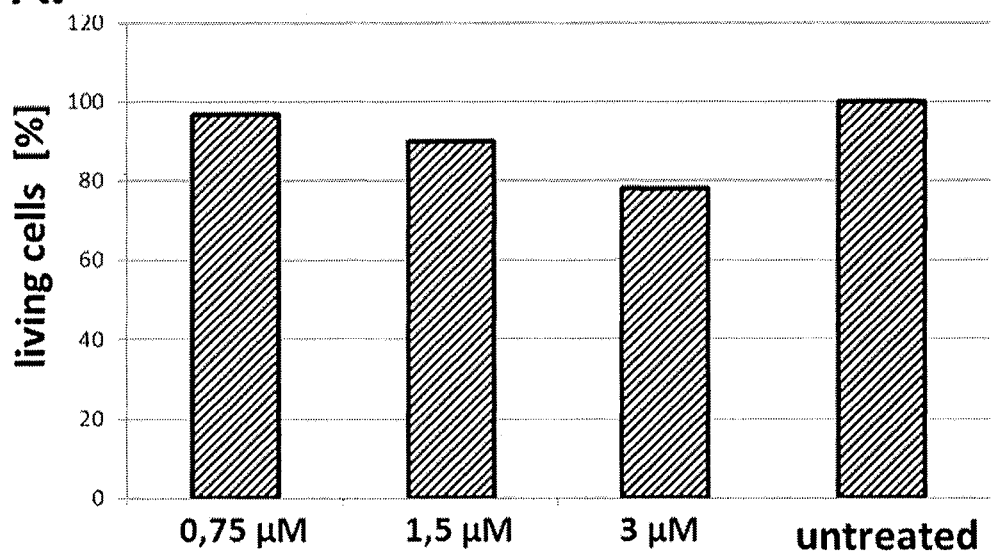
Figure 9:
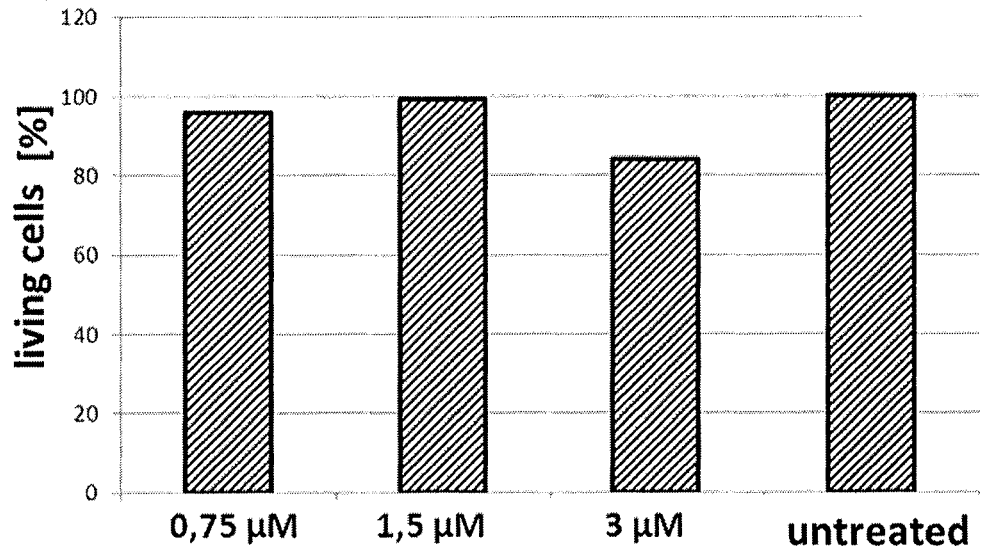

FIG. 9: Percentage of living cells after treatment with different concentrations of P005091 after "Structured treatment" (A) and "Permanent treatment" (B)

Figure 10:
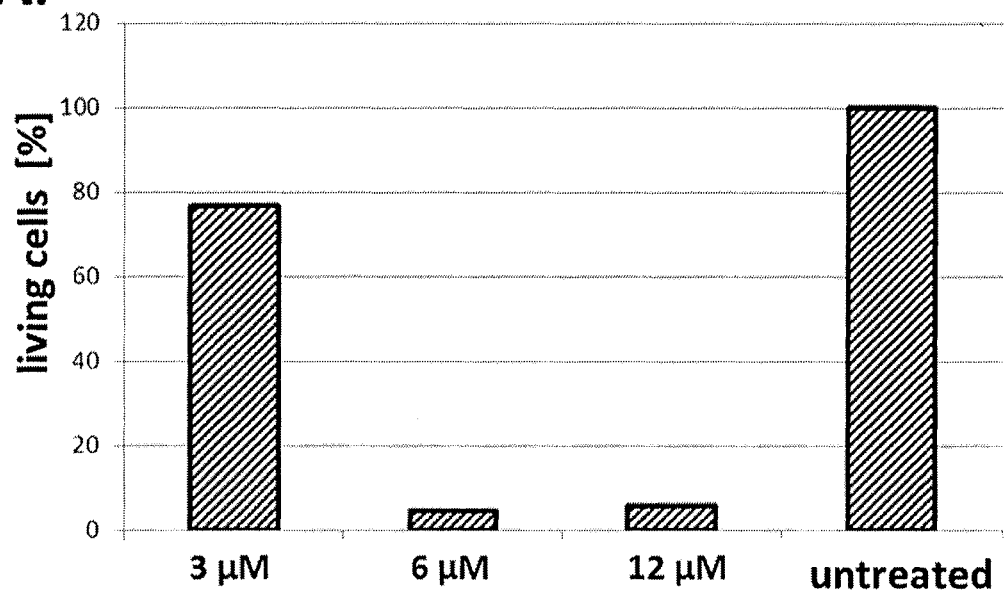
Figure 10:
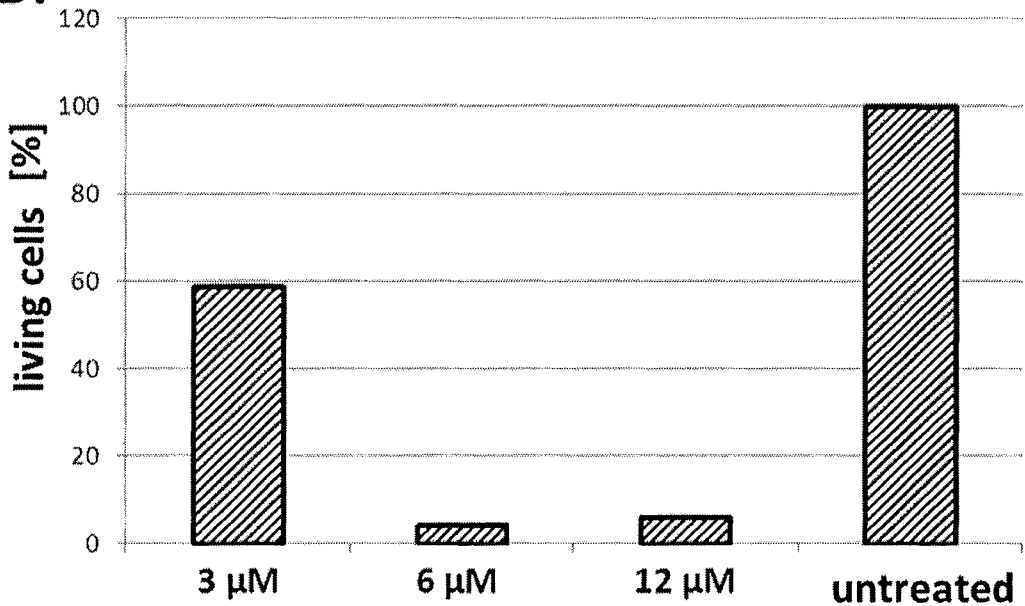

FIG. 10: Percentage of living cells after treatment with different concentrations of WP1130 after "Structured treatment" (A) and "Permanent treatment" (B)

FIG. 11: Dose-dependent enhancement of MHC-I antigen presentation after addition of the DUB inhibitor PR-619

Figure 12:
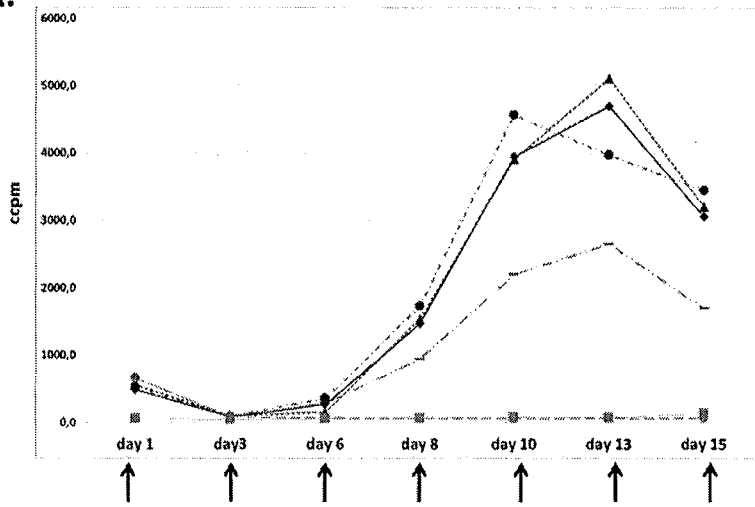
Figure 12:
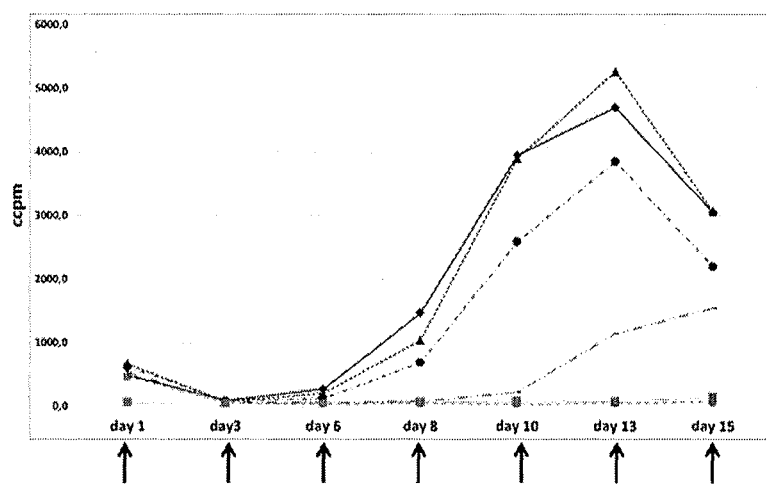
Figure 12:
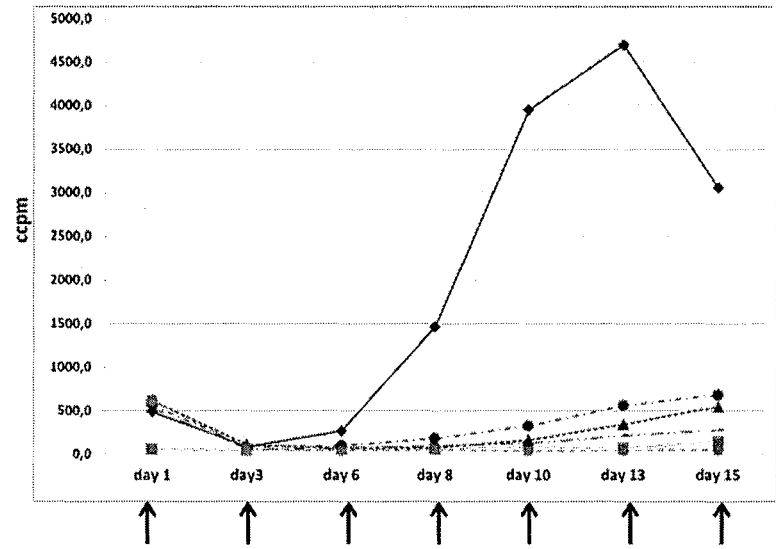

FIG. 12: "Permanent treatment" of HIV-1-infected T cells with different concentrations of bortezomib (A), PR-619 (B) and a combination of both substances (C)

12A: 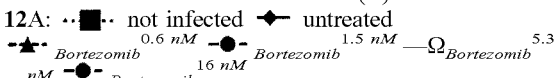

12B: 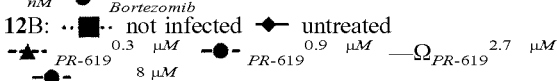

12C: 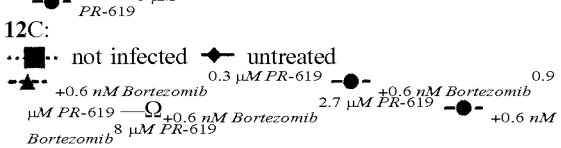

FIG. 13: Percentage of living cells after treatment with different concentrations of PR-619 (A), bortezomib (B) and a combination of both substances (C) with "Permanent treatment"

Figure 14:
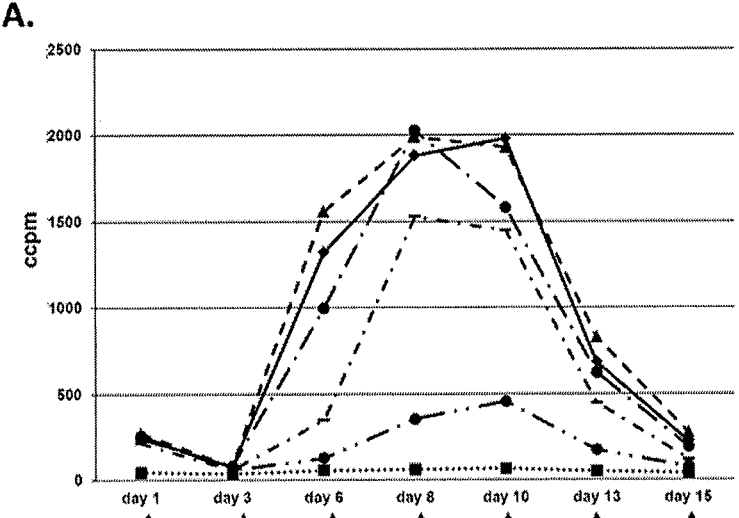
Figure 14:
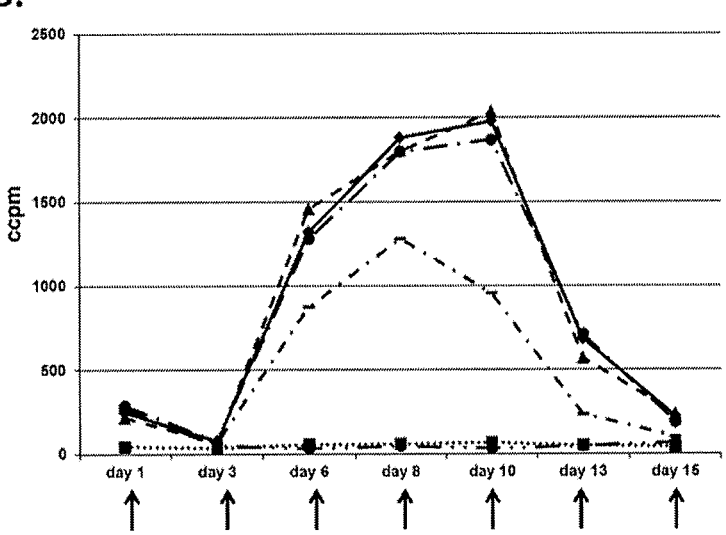
Figure 14:
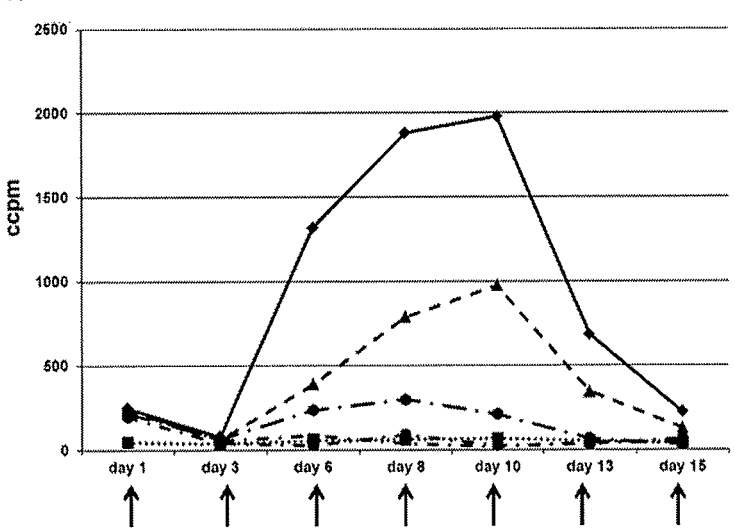

FIG. 14: "Permanent treatment" of HIV-1-infected T cells with different concentrations of PR-957 (A), PR-619 (B) and a combination of both substances (C)

14A: 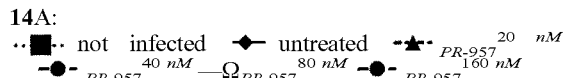

14B: 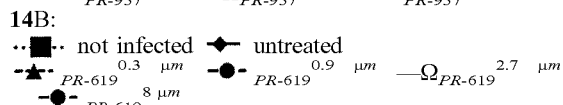

14C: 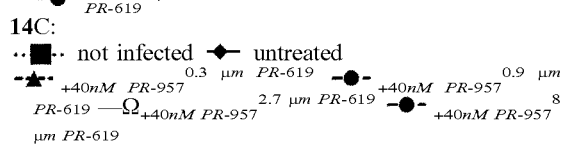

FIG. 15: Percentage of living cells after treatment with different concentrations of PR-619 (A), PR-957 (B) and a combination of both substances (C) with "Permanent treatment"

The invention claimed is:

1. A method of treating an individual having an HIV-1 infection, by administering to such individual a pharmaceutically effective amount of 2,6-diaminopyridine-3,5-bis (thiocyanate) or its pharmaceutically acceptable salts, hydrates and solvates.

2. The method of claim 1, wherein 2,6-diaminopyridine-3,5-bis(thiocyanate) or its pharmaceutically acceptable salts, hydrates and solvates is administered together with a proteasome inhibitor.

3. The method of claim 1, wherein 2,6-diaminopyridine-3,5-bis(thiocyanate) or its pharmaceutically acceptable salts, hydrates and solvates is administered together with bortezomib.

* * * * *